(12) United States Patent
Smith et al.

(10) Patent No.: US 9,133,486 B2
(45) Date of Patent: Sep. 15, 2015

(54) HYDROGENASE FUSION PROTEIN FOR IMPROVED HYDROGEN PRODUCTION

(71) Applicant: The Board of Trustees of the Leland Stanford Junior University, Palo Alto, CA (US)

(72) Inventors: Phillip Richard Smith, Yardley, PA (US); James R. Swartz, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 13/791,550

(22) Filed: Mar. 8, 2013

(65) Prior Publication Data

US 2013/0273628 A1    Oct. 17, 2013

Related U.S. Application Data

(60) Provisional application No. 61/609,477, filed on Mar. 12, 2012.

(51) Int. Cl.
| | |
|---|---|
| *C12N 9/02* | (2006.01) |
| *C12P 3/00* | (2006.01) |
| *C07K 19/00* | (2006.01) |
| *C07K 14/33* | (2006.01) |
| *C07K 14/195* | (2006.01) |
| *C12N 9/96* | (2006.01) |

(52) U.S. Cl.
CPC .................. *C12P 3/00* (2013.01); *C12N 9/0067* (2013.01); *C12N 9/0095* (2013.01); *C12N 9/96* (2013.01); *C12Y 112/07002* (2013.01); *C12Y 118/01002* (2013.01); *C07K 2319/00* (2013.01)

(58) Field of Classification Search
None
See application file for complete search history.

(56) References Cited

U.S. PATENT DOCUMENTS

2003/0109000 A1*  6/2003  Moore et al. ................. 435/69.1
2012/0077242 A1   3/2012  Swartz et al.

FOREIGN PATENT DOCUMENTS

WO    WO 2009020584 A1 *  2/2009

OTHER PUBLICATIONS

Karplus et al., Structural aspects of plant ferredoxin:NADP+ oxidoreductases, Photosynth. Res., 2004, 81, 303-15.*
Hanke et al., Fd : FNR electron transfer complexes: evolutionary refinement of structural interactions, Photosynth. Res., 2004, 81, 317-27.*
Uniprot, accession No. P29166, 2011, www.uniprot.org.*
Yacoby et al., Photosynthetic electron partitioning between [FeFe]-hydrogenase and ferredoxin-NADP+-oxidoreductase (FNR) enzymes in vitro, Proc. Natl. Acad. Sci. USA, 2011, 108, 9396-9401.*
Boyer; et al., "Cell-Free Synthesis and Maturation of [FeFe] Hydrogenases", Biotechnol Bioeng (2008), 99(1):59-67.
Kuchenreuther; et al., "Cell-free H-cluster Synthesis and [FeFe] Hydrogenase Activation: All Five CO and CN—Ligands Derive from Tyrosine", PLoS One (2011), 6(5):e20346.
Kuchenreuther; et al., "High-Yield Expression of Heterologous [FeFe] Hydrogenases in *Escherichia coli*", PLoS One (2010), 5(11):e15491.
Kuchenreuther; et al., "Tyrosine, Cysteine, and S-Adenosyl Methionine Stimulate In Vitro [FeFe] Hydrogenase Activation", PLoS One (2009), 4(10):e7565.
Smith; et al., "Generation of hydrogen from NADPH using an [FeFe] hydrogenase", Intl J of Hydrogen Energy (2012), 37(3):2977-2983.
Stapleton; et al., "Development of an In Vitro Compartmentalization Screen for High-Throughput Directed Evolution of [FeFe] Hydrogenases", PLoS One (2010), 5(12):e15275.
Woodward; et al., "Enzymatic production of biohydrogen", Nature (2000), 405(6790):1014-1015.
Zhang; et al., "High-Yield Hydrogen Production from Starch and Water by a Synthetic Enzymatic Pathway", PLoS One (2007), 2(5):e456.

* cited by examiner

*Primary Examiner* — Rebecca Prouty
*Assistant Examiner* — Todd M Epstein
(74) *Attorney, Agent, or Firm* — Bozicevic, Field & Francis LLP; Pamela J. Sherwood

(57) ABSTRACT

Compositions of a fusion protein comprising a spatially tethered ferredoxin-NADP-reductase (FNR) and an active [FeFe] hydrogenase, genetic sequences encoding such fusion proteins, and methods of use thereof are provided. The fusion proteins of the invention link an FNR polypeptide to an active [FeFe] hydrogenase through a polypeptide linker. The fusion protein facilitates improved electron transfer through a ferredoxin, and allows direct electron transfer from NADPH to the hydrogenase.

13 Claims, 5 Drawing Sheets

| N-terminus | Cpl Hydrogenase (63.8 kDa) | GSA linker | AnFNR (34.1 kDa) | C-terminus |

| (GSA)n Linker Length (AA) | 15 | 24 | 36 | 45 |
|---|---|---|---|---|
| n= | 5 | 8 | 12 | 15 |
| Bp= | 45 | 72 | 108 | 135 |
| Linker MW (kDa) | 1.3 | 2.2 | 3.2 | 4.0 |

| Assay Results | | | | |
|---|---|---|---|---|
| Sample | [Soluble Protein added] (nM) | MV Reduction Rate (nmole µL⁻¹ min⁻¹) | [Active CpI] (nM) | % Active CpI |
| CpI | 3.65 | 2.80 | 0.488 | 13.4 |
| AnFNR | 1.03 | 0.00 | 0 | 0.0 |
| (GSA)₅ | 7.23 | 2.70 | 0.470 | 6.5 |
| (GSA)₈ | 6.38 | 2.74 | 0.477 | 7.5 |
| (GSA)₁₂ | 9.46 | 2.88 | 0.502 | 5.3 |
| (GSA)₁₅ | 7.19 | 3.11 | 0.541 | 7.5 |
| no DNA | 0.00 | 0.04 | 0 | 0.0 |

HYDROGENASE FUSION PROTEIN FOR IMPROVED HYDROGEN PRODUCTION

Current traditional energy technologies rely on fossil fuels. Their most significant limitations are the depletion of limited fossil fuel reservoirs, thus, making this a non-sustainable technology, and the net generation of $CO_2$ and other greenhouse gases, thereby affecting the global climate in a fundamental and uncontrollable manner. Hydrogen gas, if produced from biomass, would be a renewable energy source that is neutral with respect to the "greenhouse gas" $CO_2$ produced during combustion, liberates large amounts of energy per unit weight in combustion, and is easily converted to electricity by fuel cells.

The US current market for hydrogen is very large and is likely to grow. For example, US agriculture uses about 20 million tons of $NH_3$ fertilizer every year, and each ton of ammonia fertilizer requires about 34 million Btu worth of natural gas to provide the hydrogen for the reduction of gaseous nitrogen. The petrochemical industry also uses very large quantities of hydrogen, produced exclusively from fossil fuels with large releases of $CO_2$.

Thus, current sources of hydrogen often rely on fossil fuels as input material, and conventional means for industrial-scale $H_2$ production such as steam reformation of natural gas fall short of the environmental criteria now needed for sustainable fuels and chemicals. The use of hydrogen as a large scale fuel therefore depends, in part, on developing new hydrogen sources.

For a variety of reasons, a large fraction of recent public and private funding has been focused on the production and use of cellulosic biomass. This situation provides an important opportunity for technology that uses cellulosic hydrolysates as feedstocks to produce hydrogen. One path of particular interest is biological hydrogen production from biomass, enabled by genetically engineered microbes that express hydrogenases—enzymes that catalyze the reversible reduction of protons into $H_2$. If this hydrogen could be produced from cellulosic crops grown on marginal lands, the resulting ammonia fertilizer would be produced with minimal new $CO_2$ release and would also help to improve the productivity of neighboring land devoted to food crops.

The present invention relates to the production of hydrogen as a sustainable local feedstock.

Literature citations. Woodward et al. (2000) Enzymatic production of biohydrogen. Nature 405:1014-1015; Zhang et al. (2007) High-yield hydrogen production from starch and water by a synthetic enzymatic pathway. PLoS ONE 2: e456. Smith, Bingham, and Swartz (2011) Generation of hydrogen from NADPH using an [FeFe] hydrogenase. Intl. J of Hydrogen Energy 37(3):2977-83.

Kuchenreuther et al. (2011) PLoS One 6(5):e20346; Stapleton and Swartz (2010) PLoS One 5(12):e15275; Kuchenreuther et al. (2010) PLoS One 5(11):e15491; Stapleton and Swartz (2010) PLoS One 5(5):e10554; Kuchenreuther et al. (2009) PLoS One 4(10):e7565; Boyer et al. (2008) Biotechnol Bioeng. 99(1):59-67.

Co-pending U.S. patent application Ser. No. 13/246,542.

SUMMARY OF THE INVENTION

Compositions of a fusion protein comprising a spatially tethered ferredoxin-NADP-reductase (FNR) and an active [FeFe] hydrogenase, genetic sequences encoding such fusion proteins, and methods of use thereof are provided. The fusion proteins of the invention link an FNR polypeptide to an active [FeFe] hydrogenase through a polypeptide linker. The fusion protein facilitates improved electron transfer through a ferredoxin, and allows direct electron transfer from NADPH to the hydrogenase.

In some embodiments of the invention, a genetic sequence encoding a fusion protein of the invention is introduced into a bacterial cell, where it is expressed, where expression may be at a high level. In other embodiments the fusion protein of the invention is synthesized in a cell-free protein synthesis reaction.

In some embodiments of the invention the fusion protein of the invention, or more usually a bacterial cell lysate comprising the fusion protein of the invention, is used for the cell-free synthesis of hydrogen from glucose and cellulosic hydrolysates. In the such methods, bacterial cells are modified to express high levels of the fusion protein of the invention; and ferredoxin. The proteins may be expressed in a single cell or in separate cells, usually the ferredoxin and the fusion protein are expressed in separate cells. Desirably at least one of the bacterial cells also expresses cytochrome D oxidase.

The cells are then lysed and the lysate, which may be a crude lysate, is combined with substrate during a production phase, where $H_2$ is produced. The substrate is typically a sugar, e.g. glucose, cellulose hydrolysates, fructose, and the like, including pentose sugars capable of entering the bacterial pentose phosphate cycle. The reaction mixture may be further supplemented with one or more of niacin as a precursor to nicotinamide; a nuclease, particularly a ribonuclease, to break down nucleic acids and generate adenine; and iodoacetamide to inactivate the normal cellular glycolytic pathway and thus maximize conversion yields. Preferred reaction conditions are substantially anaerobic, however, in some embodiments, a slow $O_2$ feed may be regulated such that the $O_2$ is totally consumed by oxidative phosphorylation to provide for ATP regeneration.

In some embodiments of the invention, the fuel value productivity will be at least about $0.1$ MJ $L^{-1}$ $hr^{-1}$, at least about $0.25$ MJ $L^{-1}$ $hr^{-1}$, at least about $4$ MJ $L^{-1}$ $hr^{-1}$, or more. For each mole of glucose, 5 or more, 7.5 or more, 10 or more moles of $H_2$ may be produced.

In another aspect, the invention provides an in vitro cell-free system for the synthesis of $H_2$, the system containing cell lysates, a sugar, and proteins: (i) fusion protein of active [FeFe] hydrogenase-FNR; (ii) ferredoxin; and NADP. Desirably cytochrome D oxidase is also present. Phosphate and nucleotides may be obtained endogenously from the cell extract by enzymes present in the extract or added to the extract.

Other features and advantages of the invention will be apparent from the detailed description, and from the claims.

DETAILED DESCRIPTION OF THE EMBODIMENTS

Compositions of a fusion protein comprising a spatially tethered ferredoxin-NADP-reductase (FNR) and an active [FeFe] hydrogenase, genetic sequences encoding such fusion proteins, and methods of use thereof are provided. The fusion proteins of the invention link an FNR polypeptide to an active [FeFe] hydrogenase through a polypeptide linker. The fusion protein facilitates improved electron transfer through a ferredoxin, and allows direct electron transfer from NADPH to the hydrogenase.

The fusion protein of the invention finds use in the cell-free synthesis of hydrogen from glucose and cellulosic hydrolysates. The invention consists of an enzymatic pathway composed of the following proteins: (1) FNR-H$_2$ase fusion protein, (2) Ferredoxin; this pathway can be combined with any source of reducing equivalents delivered by NADPH. In the embodiments of the invention, these proteins are overexpressed to high levels in one or more cell cultures or in cell free protein synthesis; following overexpression, the cultures are lysed (homogenized) and combined as necessary to facilitate hydrogen production from simple sugars in a bioreactor.

In the bioreactor, the enzyme pathway functions together with an active pentose-phosphate pathway (PPP) in the E. coli extract to transfer electrons from the sugars to the [FeFe] hydrogenase. The hydrogenase combines the electrons with available protons to produce hydrogen, which is collected. Nicotinamide adenine dinucleotide phosphate (NADPH) functions as an important intermediate to transfer electrons; additional NADPH is optionally made in the bioreactor by supplementing the extracts with one or more of niacin (a common vitamin and nicotinamide precursor) and nuclease (to provide a source of adenine by breakdown of nucleic acids already in the cell extract). Additionally, iodoacetamide may be added to inactivate the normal glycolytic pathway of the bacterial cells to avoid loss of the sugars through conversion to other metabolic products and to thereby maximize conversion yields. Various C6 and C5 sugars find use, e.g. glucose, fructose, xylose, etc., and may be obtained from starch, from sucrose, from cellulose, hemicellulose or from combinations thereof.

Figure 9:
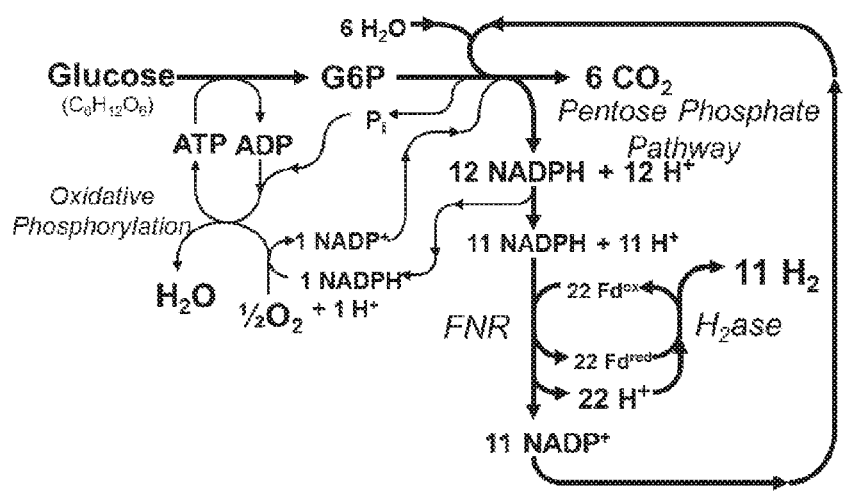
FIG. 9. Synthetic enzyme pathway for the production of hydrogen from glucose.

FIG. 9 illustrates the overall metabolic scheme for this proposal. Glucose is first converted to glucose 6-P using ATP generated by oxidative phosphorylation. The glucose 6-P enters the pentose phosphate pathway where it is converted to 6 $CO_2$'s while reducing 12 NADP's to 12 NADPH's. One NADPH is used to provide the ATP for glucose phosphorylation, and the other 11 are used for reducing equivalents for hydrogen production. The FNR moiety catalyzes the transfer of electrons from NADPH to ferredoxin (Fd).

In some embodiments, the process will utilize cell extracts in which the enzymes have been overexpressed. This enables cost effective production since no purification is required and several enzymes are provided by one organism. The enzymes that constitute the pentose phosphate pathway are present in the extracts and do not require overexpression.

Definitions

Fusion protein. The term "fusion protein" as used herein refers to a hybrid polypeptide which comprises protein domains from at least two different proteins. For the purposes of the invention, an active hydrogenase domain, usually an Fe-Fe hydrogenase, is linked through a peptide bond at its carboxy terminus to a flexible amino acid linker, which is linked through a peptide bond at its carboxy terminus to the amino terminus of an active ferredoxin-NADP-reductase (FNR), as exemplified in FIG. 1 and the specific sequences set forth IN SEQ ID NO:1-8.

As is known in the art, conveniently a fusion protein is created by recombinant methods, where the coding sequence of the hydrogenase is operably linked to the linker sequence, and the linker sequence to the genetic sequence encoding the FNR. The coding sequence of the fusion protein is operably linked to regulatory sequences for control of transcription and translation as appropriate for the expression system, e.g. bacterial cell, CFPS, and the like.

Hydrogenase. Hydrogenases catalyse the reversible oxidation/reduction of molecular hydrogen ($H_2$) and play a vital role in anaerobic metabolism. Hydrogen oxidation is coupled to the reduction of electron acceptors such as oxygen, nitrate, sulphate, carbon dioxide and fumarate, whereas proton reduction ($H_2$ evolution) is coupled to molecules such as ferredoxin. The methods of the invention may be applied to any of the Fe-Fe hydrogenases that accept electrons from ferredoxin.

In one embodiment, the term "hydrogenase" as used herein refers to an enzyme that meets one or more of the criteria provided herein. Using these criteria, one of skill in the art can determine the suitability of a candidate enzyme for use in the methods of the invention. Many enzymes will meet multiple criteria, including two, three, four or more of the criteria, and some enzymes will meet all of the criteria. The terms "hydrogenase" can refer to a full length enzyme or fragment thereof with the capability of catalyzing hydrogen oxidation/reduction.

Hydrogenases of the invention include enzymes having at least about 20% sequence identity at the amino acid level, more usually at least about 40% sequence identity, and may have at least about 70%, 80% or 90% sequence identity to one of the following hydrogenases: *Chlamydomonas reinhardtii* iron-iron-hydrogenase (Genbank accession AY055756); *Clostridium pasteurianum* hydrogenase (Genbank accession AAA23248.1); *Megasphaera elsdenii* hydrogenase (Genbank accession AF120457); *Desulfovibrio vulgaris* hydrogenase (Genbank accession CAA26266.1). For example, see Forestier et al. (2003) Eur. J. Biochem. 270 (13), 2750-2758; Meyer et al. (1991) Biochemistry 30:9697-9704; Voordouw et al. (1985) Eur. J. Biochem. 148:515-520; Atta et al. (2000) Biochim Biophys Acta. 1476(2):368-71; Fauque et al. (1988) FEMS Microbiol. Rev. 4, 299-344; Cammack et al. (1994) Methods Enzymol. 243, 43-68; and de Lacey et al. (1997) J. Am. Chem. Soc. 119, 7181-7189, each herein incorporated by reference.

Homology-based identification (for example, by a PILEUP sequence analysis) of enzymes can be routinely performed by those of skill in the art upon contemplation of this disclosure to identify those suitable for use in the methods of the present invention. Such enzymes are usually produced in microorganisms, particularly bacteria. Hydrogenases of the invention also include an enzyme belonging to the enzyme classifications EC 1.12.7.2 and EC 1.12.2.1.

The nucleic acid sequences encoding the above hydrogenases may be accessed from public databases as previously cited. Identification of additional hydrogenases is accomplished by conventional screening methods of DNA libraries or biological samples for DNA sequences having a high degree of similarity to known hydrogenase sequences.

Hydrogenases of interest include, without limitation, [FeFe] hydrogenases that primarily catalyze $H_2$ evolution, e.g. *Chlamydomonas reinhardtii* [FeFe]-hydrogenase; *Clostridium pasteurianum* hydrogenase; *Megasphaera elsdenii* hydrogenase; derivatives; variants; homologs; mutants; and the like.

In some embodiments of the invention, the iron-iron hydrogenase is derived from a *Clostridium* species. Hydrogenases of interest include, without limitation, those found in the species *Clostridium botulinum; Clostridium tyrobutyricum; Clostridium perfringens; Clostridium butyricum; Clostridium saccharobutylicum; Clostridium novyi; Clostridium pasteurianum; Clostridium acetobutylicum; Clostridium cellulovorans; Clostridium paraputrificum; Clostridium kluyveri*DSM 555; *Clostridium papyrosolvens*, etc. and the related species *Alkaliphilus metalliredigens, Eubacterium acidaminophilum, Anaerocellum thermophilum, Caldicellulosiruptor saccharolyticus* etc.

For the purposes of the present invention, an active fragment of a [FeFe] hydrogenase, i.e. a fragment that confers substantially all of the enzymatic activity of the native protein, e.g. at least about 50% of the activity, at least about 75%, at least about 80%, at least about 90%, at least about 95%, when measured under standard conditions, will be used.

The active fragment may comprise all or a part of a native hydrogenase sequence (amino acid or polynucleotide coding sequence), usually at least about 50%, at least about 75%, at least about 80%, at least about 85%, at least about 90%, at least about 95%, up to the complete coding or amino acid sequence.

Linker. The sequence between the two active domains, i.e. the hydrogenase and FNR, is a short polypeptide of from 4 to 40 amino acids in length, and can be from about 5 to about 20, from about 5 to about 15, from about 5 to about 12 or 8 amino acids in length. The linker used to link the two domains can comprise any amino acid sequence that does not substantially hinder interaction of the domains with their respective substrates.

Linker sequences vary greatly in length and amino acid sequence, but are usually similar in amino acid composition (rich in polar, uncharged, and/or small amino acids). Flexible linkers allow the connecting domains to freely twist and rotate through space to recruit their binding partners or for those binding partners to induce larger scale interdomain conformation changes.

Once the length of the amino acid sequence has been selected, the sequence of the linker can be selected, e.g., by using naturally occurring or synthetic linker sequences as a scaffold (e.g., GTGQKP and GEKP, see Liu et al., Proc. Nat'l Acad. Sci. U.S.A. 94:5525-5530 (1997); see also Whitlow et al., Methods: A Companion to Methods in Enzymology 2:97-105 (1991)) or by evaluating various linker candidates for their effects on fusion protein activity. Preferred amino acid residues for linkers of the present invention include, but are not limited to glycine, alanine, leucine, serine, valine and threonine. Typically, the linkers of the invention are made by making recombinant nucleic acids encoding the linker and the active domains, which are fused via the linker amino acid sequence.

Exemplary amino acid sequences include GSA repeats, poly-alanine, poly-glycine, LAA repeats, LGGGGSGGGGSGGGGSAAA (SEQ ID NO: 9), LAE-AAAKEAAAKEAAAKAAA (SEQ ID NO: 10), LAE-AAAKEAAAKAAA (SEQ ID NO: 11), LSGGGGSGGGGSGGGGSGGGGSAAA (SEQ ID NO: 12), LAEAAAKEAAAKEAAAKEAAAKAAA (SEQ ID NO: 13), $G_4S$ repeats, and the like, for example see Arai et al. Protein Eng. (2001) 14 (8): 529-532.

Ferredoxin-NADP-reductase (FNR), EC 1.18.1.2, may be obtained from any suitable source, including *E. coli, Anabaena* sp., and the like, including FNR from photosynthetic organisms such as higher plants, e.g. *Spinacea oleracea* (spinach).

In photosynthetic organisms, FNR is the last enzyme in the transfer of electrons during photosynthesis from photosystem I to NADPH. In such organisms it is a soluble protein that is found both free in the chloroplast stroma and bound to the thylakoid membrane. This binding occurs opposite to the active site of the enzyme and does not seem to affect the structure of the active site or have a significant impact on the enzyme's activity. In the plant-like family of FNRs, selective evolutionary pressure has led to differences in the catalytic efficiency of FNRs in photosynthetic and nonphotosynthetic organisms. Electron transfer by FNR is a rate limiting step in photosynthesis, so the plastidic FNR in plants have evolved to be highly efficient. These plastidic FNRs are 20-100 fold more active than bacterial FNRs.

In nonphotosynthetic organisms, the FNR primarily works in reverse to provide reduced ferredoxin for various metabolic pathways. These pathways include nitrogen fixation, terpenoid biosynthesis, steroid metabolism, oxidative stress response, and iron-sulfur protein biogenesis.

For the purposes of the present invention, an active fragment of FNR, i.e. a fragment that confers substantially all of the enzymatic activity of the native protein, e.g. at least about 50% of the activity, at least about 75%, at least about 80%, at least about 90%, at least about 95%, when measured under standard conditions, will be used.

The active fragment may comprise all or a part of a native FNR sequence (amino acid or pooynucleotide coding sequence), usually at least about 50%, at least about 75%, at least about 80%, at least about 85%, at least about 90%, at least about 95%, up to the complete coding or amino acid sequence.

Ferredoxin. Ferredoxins of interest include, without limitation, *Clostridium pasteurianum* ferredoxin; *Synechocystis* ferredoxin, *E. coli* ferredoxin, *Spinacia oleracea* ferredoxin; *Anabaena* ferredoxin, derivatives; variants; homologs; mutants; and the like. Included, without limitation, are $Fe_2S_2$, and $Fe_4S_4$ ferredoxins. A candidate ferredoxin may be assayed for $H_2$ production with a hydrogenase and/or FNR of interest, and may be evolved to optimize activity. The ferredoxin may be synthesized in a cell with the hydrogenase.

As used herein, "in vitro reaction" refers to a reaction performed in a controlled environment (e.g., an experimental environment or an environment outside a living organism).

As used herein, "cell-free" refers to a non-living system, e.g., in vitro or ex vivo systems containing cellular components. Sources for the components of cell-free systems include cell extracts and lysates, usually a crude cell lysate.

As used herein a crude cell lysate comprises the lysate of a population of cells, which is substantially free of intact cells; and which is usually not subjected to enrichment techniques such as chromatography, dialysis, and the like. Such a cell lysate may or may not be clarified by such means as centrifugation or filtration. Cell-free systems are able to reconstitute cellular reactions, e.g., enzymatic and metabolic pathways. A cell lysate, usually a crude cell lysate, is obtained from cells expressly engineered to synthesize one or more proteins of interest, which results in the generation of a compound of $H_2$.

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A "coding sequence" or a sequence which "encodes" a selected polypeptide, is a nucleic acid molecule which is transcribed (in the case of DNA) and translated (in the case of mRNA) into a polypeptide, for example, in a cell-free polypeptide synthesis reaction; or in vivo when placed under the control of appropriate regulatory sequences (or "control elements"). The boundaries of the coding sequence are typically determined by a start codon at the 5' (amino) terminus and a translation stop codon at the 3' (carboxy) terminus. A transcription termination sequence may be located 3' to the coding sequence. Other "control elements" may also be associated with a coding sequence.

"Operably linked" refers to an arrangement of elements wherein the components so described are configured so as to perform their usual function. Thus, a given promoter that is operably linked to a coding sequence (e.g., a reporter expression cassette) is capable of effecting the expression of the coding sequence when the proper enzymes are present. The promoter or other control elements need not be contiguous with the coding sequence, so long as they function to direct the expression thereof. For example, intervening un-translated yet transcribed sequences can be present between the promoter sequence and the coding sequence and the promoter sequence can still be considered "operably linked" to the coding sequence.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning and expression vehicles, as well as integrating vectors.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "polypeptide" is used in it broadest sense to refer to a compound of two or more subunit amino acids, amino acid analogs, or other peptidomimetics. The subunits may be linked by peptide bonds or by other bonds, for example ester, ether, etc. As used herein, the term "amino acid" refers to either natural and/or unnatural or synthetic amino acids, including glycine and both the D or L optical isomers, and amino acid analogs and peptidomimetics.

Extract organism. As described above, the coding sequence for the fusion protein and/or ferredoxin proteins are present or introduced into the source organism, and may be present on a replicable vector or inserted into the source organism genome using methods well-known to those of skill in the art. Such vector sequences are well known for a variety of bacteria. The expression vector may further comprise sequences providing for a selectable marker, induction of transcription, etc.

The coding sequences are operably linked to a promoter sequence active in the organism. Promoters are untranslated sequences located upstream (5') to the start codon of a structural gene (generally within about 100 to 1000 bp) that control the transcription and translation of a particular nucleic acid sequence. Promoters may be constitutive or inducible, where inducible promoters initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to protein-encoding DNA by removing the promoter from the source DNA, e.g. by PCR amplification of the sequence, etc. and inserting the isolated sequence into the vector. Both the native hydrogenase promoter sequence and many heterologous promoters may be used for expression, however, heterologous promoters are preferred, such as T7, as they generally permit greater transcription and higher yields. Promoters suitable for use with prokaryotic hosts include the β-lactamase and lactose promoter systems; alkaline phosphatase; a tryptophan (trp) promoter system; an arabinose promoter system; and hybrid promoters such as the tac promoter. However, other known bacterial and bacteriophage promoters are suitable. Their nucleotide sequences have been published, thereby enabling a skilled worker operably to ligate them to DNA encoding the $H_2$ pathway proteins.

Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis*, *Pseudomonas* such as *P. aeruginosa*, and *Streptomyces*.

Host cells are transfected and preferably transformed with the above-described expression or cloning vectors and cultured in conventional nutrient media modified as appropriate for inducing promoters, selecting transformants, and preparing extracts as set forth in the Examples.

In other embodiments of the invention, the fusion protein is synthesized in a cell-free synthesis reaction, and may be performed as described for hydrogenase in U.S. Pat. No. 7,351,563. In such reactions, one or more maturase enzymes may be included in the cell extract or added to the reaction. Additionally FAD may be added at a concentration of from about 10 to about 250 μM, e.g. around about 100 μM.

Sugar. As used herein, the term refers to a number of carbohydrates, such as monosaccharides, disaccharides, oligosaccharides, and polysaccharides, usually pentose or hexose sugars or polymers thereof. Monosaccharides that find use include, without limitation, fructose, arabinose, lyxose, ribose, xylose, ribulose, xylulose, deoxyribose, allose, altrose, glucose, mannose, gulose, idose, galactose, talose. Disaccharides may include sucrose, lactose, maltose, etc. Polysaccharides may include starches, glycogen, cellulose, pectin, peptidoglycan, lipopolysaccharides, capsules, exopolysaccharides, and the like. Sugars may be phosphorylated, e.g. glucose-6-phosphate, etc. Sugars may be included in the reaction mix at a concentration sufficient to provide energy for $H_2$ evolution, e.g. from about 1 mM to about 1000 mM, and may be about 5 mM, 10 mM, 25 mM, 50 mM, 75 mM, 100 mM, 250 mM, 500 mM, 750 mM, 1000 mM, and may also be supplied by continuous addition.

Reaction mix: as used herein refers to a reaction mixture capable of catalyzing the synthesis of $H_2$ from sugar, which sugar may be a phosphorylated or non-phosphorylated sugar. The reaction mixture comprises extracts from bacterial cells, and the synthesis is performed under substantially anaerobic conditions. The volume percent of extract in the reaction mix will vary, where the extract is usually at least about 10% of the total volume; more usually at least about 20%; and in some instances may provide for additional benefit when provided at least about 50%; at least about 60%; or at least 75% of the total volume. In certain industrial applications the volume percent of extract may be around about 90% or higher. The reaction mixture may be further supplemented with one or more of niacin, nicotinamide, NAD, etc., usually at a concentration of from about 0.1 mM to 10 mM, e.g. at about 0.5 mM, about 1.0 mM, about 4 mM, etc. as a precursor or source of NAD and NADP; a nuclease, particularly a ribonuclease, which may be used at a conventional dose for example from about 0.5 µg/ml to about 50 µg/ml or higher, to break down nucleic acids and generate adenine; and an agent to inactivate the endogenous microbial cell glycolytic pathway and thus maximize conversion yields.

Useful inactivating agents include iodoacetamide, N-ethyl maleimide, iodoacetate, N-iodoacetyl-N'-(5-sulfonic-1-naphthyl)ethylene diamine, etc., as known in the art; especially those compounds including iodoacetamides, maleimides, benzylic halides and bromomethylketones. The concentration of inactivation agent and length of time for the reaction will be determined by the specific compound that is chosen. The inactivation agent is added at a concentration that substantially eliminates the endogenous cellular glycolytic pathway activity. As an example, where the inactivation agent is iodoacetamide, it may be added at a concentration of from about 10 to about 50 µM, and incubated from between 15 to 60 minutes.

Before describing the present invention in detail, it is to be understood that this invention is not limited to particular formulations or method parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

PRODUCTION METHODS

Production of $H_2$ is accomplished by providing a cell lysate from a cell in which the fusion protein of the invention are expressed, optionally in combination with ferredoxin, or in a mixed lysate with a cell expressing ferredoxin; or the unpurified product of a CFPS reaction. The turnover number (TON) for the FNR domain of the fusion protein of the invention in such a reaction mixture may be at least about 10 $sec^{-1}$, at least about 15 $sec^{-1}$, at least about 25 $sec^{-1}$, at least about 40 $sec^{-1}$, at least about 75 $sec^{-1}$, at least about 100 $sec^{-1}$, or more. The volume production of $H_2$ (mmol $H_2L^{-1}$ $hr^{-1}$) in such a reaction may be 2.5, at least about 5, at least about 7.5, at least about 10, at least about 50 or more in a reaction mix comprising a sugar and a ferredoxin.

During cell culture it may be desirable to control the components of the growth medium and culturing conditions of the cells in order to avoid exposure of the hydrogenase to conditions that affect activity, e.g. exposure to $O_2$ and the like. For production purposes, a lysate of the cell can be utilized. Cells are lysed by any convenient method that substantially maintains enzyme activity, e.g. sonication, French press, and the like as known in the art. The lysate may be fractionated, particulate matter spun out, etc., or may be used in the absence of additional processing steps. The cell lysate may be further combined with substrates, co-factors and such salts, buffers, etc. as are required for activity, and may be treated with iodoacetamide or a similar agent. Substrates will usually include glucose or another suitable sugar, a source of nicotinamide, and a source of ATP or adenine.

Lysates of cells of different genetic backgrounds, e.g. previously altered or genetically engineered, or species, or that are prepared by different strategies can be mixed and simultaneously or sequentially used in a bioprocess with the cell lysate of the invention. The lysate can be free or immobilized, and can be reused or disposed at each stage of the process.

The reactions may utilize a large scale reactor, small scale, or may be multiplexed to perform a plurality of simultaneous syntheses. Continuous reactions will use a feed mechanism to introduce a flow of reagents, and may isolate the end-product as part of the process. Batch systems are also of interest, where additional reagents may be introduced over time to prolong the period of time for active synthesis or to limit the production of side products. A reactor may be run in any mode such as batch, extended batch, semi-batch, semi-continuous, fed-batch and continuous, and which will be selected in accordance with the application purpose.

The reactions may be of any volume, either in a small scale, usually at least about 1 ml and not more than about 15 ml, or in a scaled up reaction, where the reaction volume is at least about 15 ml, usually at least about 50 ml, more usually at least about 100 ml, and may be 500 ml, 1000 ml, or greater up to many thousands of liters of volume. Reactions may be conducted at any scale.

Various salts and buffers may be included, where ionic species are typically optimized with regard to product production. When changing the concentration of a particular component of the reaction medium, that of another component may be changed accordingly. Also, the concentration levels of components in the reactor may be varied over time. The adjuster of the thiol/disulfide oxidation/reduction potential may be dithiothreitol, ascorbic acid, glutathione and/or their oxidized forms. Other adjusters of the general redox potential may also be used.

In a semi-continuous operation mode, the reactor may be operated in dialysis, diafiltration batch or fed-batch mode. A feed solution may be supplied to the reactor through the same membrane or a separate injection unit. The gaseous products, hydrogen and $CO_2$, may be removed in a stream of an anoxic carrier gas such as nitrogen. The reactor may be stirred internally or by proper agitation means, including by gas sparging. The amount of hydrogen produced can be determined using gas flow meters and any instrument that measures the % $H_2$ in the gas, such as a gas chromatograph. The hydrogen can then be removed from the $CO_2$ and carrier gas by any convenient means, as known in the art.

For industrial scale production of hydrogen from glucose a single set of large cell extract production fermenters (for example, a 60,000 liter and a 150,000 liter fermenter) would supply the enzyme mix (cell extract) for several (most likely 3 to 5) hydrogen bioreactors. *E coli* grows rapidly requiring roughly 12 hours to reach high cell density (about 200 g/l) and another 8 to 10 hours to express the enzymes required for hydrogen production. This cell suspension may be passed directly through a high pressure homogenizer and into a hydrogen production vessel. Assuming the cell extract would retain acceptable activity for 3 days, one cell production fermenter would supply three hydrogen bioreactors. The $N_2$ required for gas circulation in the hydrogen bioreactors may be obtained from the off-gas of the aerobic fermentation during a microaerobic incubation. By feeding air at a lower rate, the dissolved oxygen concentration will go essentially to zero to induce the high affinity cytochrome oxidase (cytochrome d oxidase) needed for the oxidative phosphorylation in the hydrogen reactor. During this period, the organism will strip all of the oxygen from the air, replacing it with $CO_2$ which will be removed to leave essentially pure nitrogen.

After the cells are lysed, e.g. by a single pass through the high pressure homogenizer, the resultant cell extract may be directly transferred into the hydrogen bioreactor, treated with iodoacetamide to inactivate the EMP pathway and supplemented with NADP and FAD as required. Antifoaming agents may be added, and the oxygen-free nitrogen obtained from the microaerobic fermentation can be circulated through the bioreactor to harvest the hydrogen. The hydrogen may be removed with nanoporous inorganic membrane devices.

The hydrogen thus obtained may be pressurized and transferred directly to a local consumer such as an ammonia fertilizer producer, a cement producer, or a petrochemical plant. Alternatively, storage and transportation technology may be utilized for broader distribution. The $CO_2$ may be removed by semi-permeable membrane, and the like, and can be sequestered or sold.

In the hydrogen bioreactors, sugar concentrations and hydrogen production will be monitored to adjust sugar feed rates to optimal levels and to decide when the reactor needs to be recharged with new cell extract. (The waste extract could then be sold as fertilizer for local farms.) Nitrogen gas would be circulated to maintain a low hydrogen partial pressure to encourage rapid hydrogen formation. A small feed of air would be added at the gas inlet of each reactor to provide the oxygen required for ATP generation. This rate would also be controlled at the optimal level based on metabolite measurements.

It is to be understood that this invention is not limited to the particular methodology, protocols, cell lines, animal species or genera, constructs, and reagents described, as such may, of course, vary. It is also to be understood that the terminology used herein is for the purpose of describing particular embodiments only, and is not intended to limit the scope of the present invention, which will be limited only by the appended claims.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the cell lines, constructs, and methodologies that are described in the publications that might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

Figures 1, 2, 3:
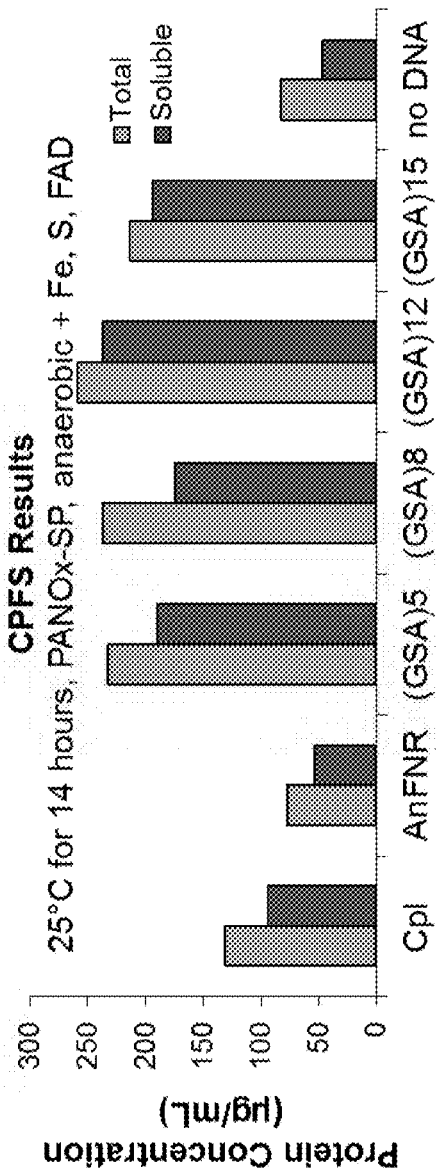
FIG. 1. Design of CpI-AnFNR Fusion Protein.
FIG. 2. Details of the Linkers Used in the Four Fusion Proteins.
FIG. 3. Protein yields for the four fusion proteins as well as positive controls (CpI, AnFNR) and negative control (no DNA).

A CpI Hydrogenase-FNR Fusion Protein Offers Greatly Improved Hydrogen Production Rates Through a Synthetic Enzyme Pathway A fusion protein composed of the [FeFe] hydrogenase from *Clostridium pasteurianum* (CpI) and the ferredoxin-NADPH-reductase from *Anabaena variabilis* (AnFNR) was created. The enzymes are connected by (GSA)$_n$ linker, where GSA denotes a repeating 3 amino acid sequence consisting of n glycine-serine-alanine repeats. This linker serves to tether the two enzymes, which greatly enhances their combined enzymatic activity. Only one specific arrangement of the enzymes is possible, because the C-terminal tyrosine of the AnFNR plays an essential role in the AnFNR active site. This arrangement is shown in FIG. 1. Four linker lengths between the N-terminus of the AnFNR and the C-terminus of the CpI hydrogenase were tested. The details of the linkers are presented in FIG. 2.

This fusion protein replaces two proteins in a synthetic enzyme pathway (see FIG. 9). The pathway functions to transfer reducing equivalents from biomass sugars to the CpI hydrogenase. FNR plays an essential role in this pathway by accepting electrons from NADPH, the output of the pentose phosphate pathway (PPP), and transferring them to ferredoxin. The ferredoxin, which is an electron shuttle, delivers the electrons to the CpI hydrogenase for hydrogen production. Previous work with this pathway identified the AnFNR and the 2[4Fe4S] ferredoxin from *Clostridium pasteurianum* (CpFd, which is the native electron donor for the CpI hydrogenase and a two electron-carrying ferredoxin), as the best pair of proteins for use in this pathway. However, the observed reaction rate of the pathway was much lower than that suggested by the observed rates of the individual enzymes (FNR and the CpI hydrogenase). Given the nature of the ferredoxin binding to each protein (ion pairing of the highly negative CpFd to patches of positive charge on the surfaces of the AnFNR and CpI), it was hypothesized that the fusion of the two proteins may facilitate the formation of a ternary complex between AnFNR, CpI, and CpFd, which would create a conduit for direct electron transfer. Alternatively, bringing the two proteins closer together may facilitate faster kinetics by reducing the time required for the CpFd to diffuse between the two proteins. However, at the outset of this work it was unknown if connecting these two complicated proteins in this way would have a beneficial effect or if both would be inactive in this arrangement. The final DNA and protein sequences for the four fusion proteins are included in appendix A.

The following example demonstrates much improved hydrogen production rates with four fusion proteins, relative to rates previously observed with the unattached enzymes.

Example 1

Figure 6:
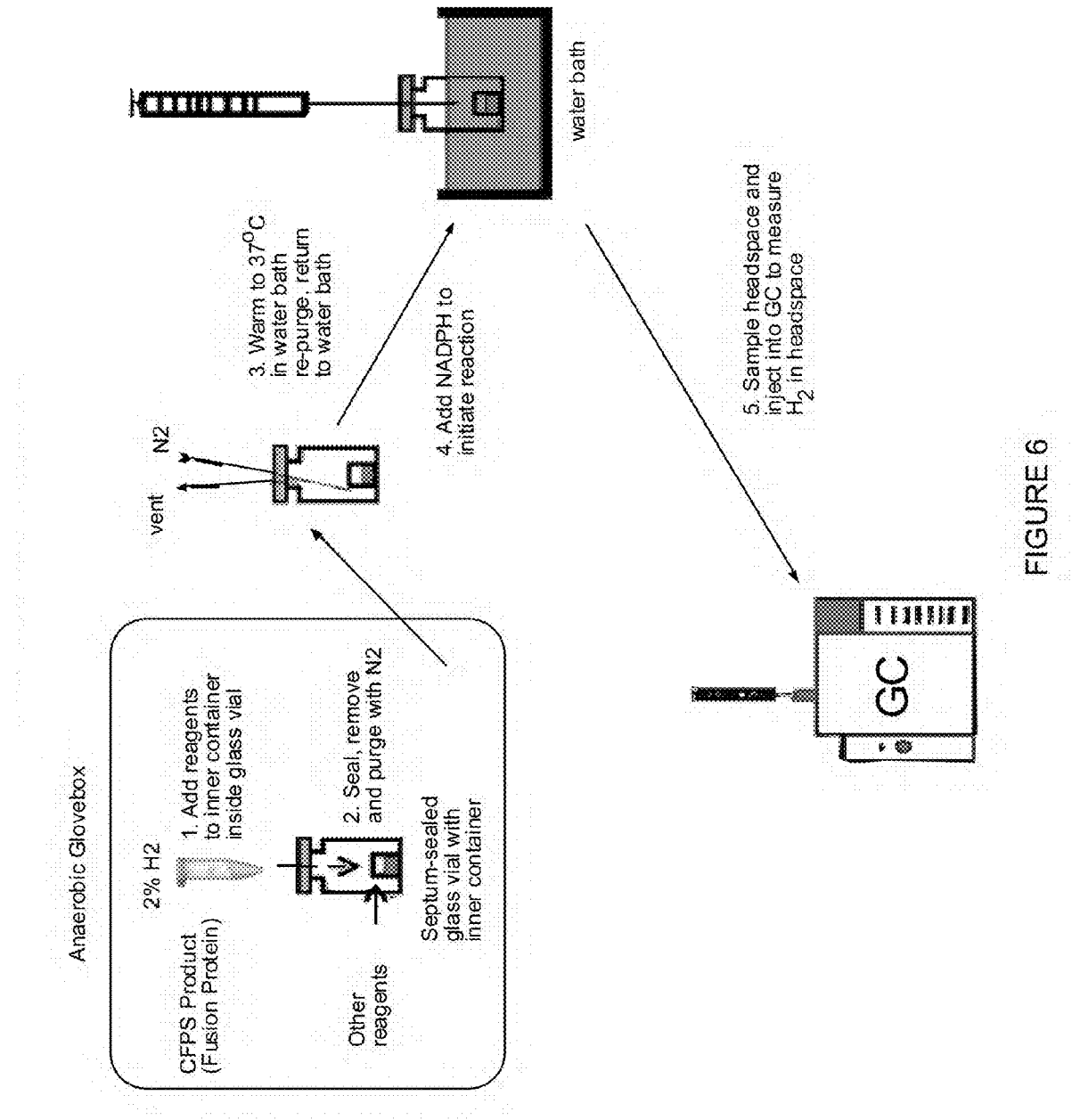
FIG. 6. Procedure for preparing the hydrogen production reactions and measuring hydrogen produced.

Production of Four CpI-AnFNR Fusion Proteins by Cell-Free Protein Synthesis (CFPS) and Characterization of Specific Hydrogen Production Activity The four CpI-AnFNR fusion proteins were expressed via CFPS from linear DNA templates, using the PANOx-SP protocol, with modifications to facilitate production of active CpI hydrogenase and FNR. These modifications included the use of a reconstituted cell extract containing the maturases HydE, F, and G, as well as general overexpression of the isc operon. Additionally, 50 µM FAD was added to facilitate activation of the AnFNR, as it requires an FAD cofactor in the active site. Radiolabeled $^{14}C$ leucine was included in the CFPS reactions to facilitate measurement of protein yield by liquid scintillation counting and visualization of the protein via an autoradiogram following SDS-PAGE analysis (see FIG. 6). CFPS yields are shown in FIG. 3.

The activities of the proteins thus produced were characterized with two spectrophotometric assays, as described below.

The methyl viologen assay. The methyl viologen (MV) assay is a standard assay for measuring the activity of hydrogenases (see Equation 1). The hydrogenase oxidizes hydrogen and reduces MV, which is blue in its reduced state. The absorbance at 580 nm is measured over time and used with the MV extinction coefficient (9780 $M^{-1}$ $cm^{-1}$) to calculate the rate of reaction with the Beer-Lambert law. The known specific activity of the hydrogenase (450 µmole $H_2$ consumed $min^{-1}$ mg $CpI^{-1}$) in this assay is then used to determine the amount of active protein present in the sample. The rate of MV reduction and corresponding concentration of active hydrogenase are presented in FIG. 4.

(Equation 1)

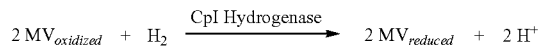

$$2\,MV_{oxidized} + H_2 \xrightarrow{\text{CpI Hydrogenase}} 2\,MV_{reduced} + 2\,H^+$$

Figures 4, 5:
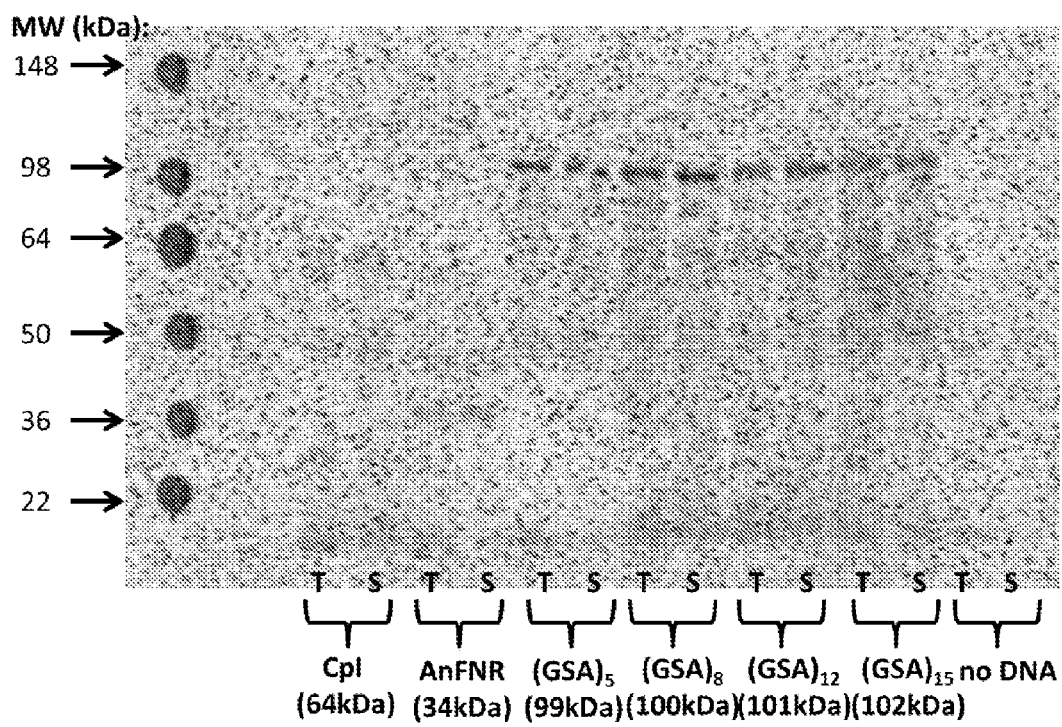
FIG. 4. Active CpI concentrations determined from the MV assay.
FIG. 5. Autoradiogram of a SDS-PAGE analysis of the fusion proteins and positive and negative controls. The band representing the fusion proteins ran in the gel at around 100 kDa, indicating successful production of full-length fusion protein. 'T' denotes total protein, while 'S' denotes soluble protein.

NADP$^+$ reduction assay. This assay measured the activity of both the AnFNR and CpI hydrogenase enzymes (see diagram of electron flow in Equation 2). With the CpFd added to serve as an electron shuttle, the reduction of NADP$^+$ to NADPH by the AnFNR was coupled to the oxidation of hydrogen by the CpI hydrogenase. This assay is the reverse of the hydrogen production reaction, but is done in an anaerobic glovebox (with is maintained at a 2% hydrogen atmosphere, which supplies the hydrogen for the assay). The assay is tracked spectrophotometrically by monitoring the increase in absorbance at 340 nm, due to the formation of NADPH, over time. The rate of formation of NADPH is calculated using the NADPH extinction coefficient (6270 $M^{-1}cm^{-1}$) and the Beer-Lambert law. This rate is shown in FIG. 5, as well as the concentration of active FNR, determined by using the specific activity previously determined by us for CFPS-produced and purified AnFNR (8 nmole NADPH nmole AnFNR$^{-1}$ sec$^{-1}$; determined using the cytochrome C assay. This provides a reasonable estimate of the FNR specific activity but assumes similar activity while catalyzing electron transfer in either direction. The assay also takes advantage of the much higher CpI potential turnover numbers such that FNR is the rate limiting enzyme.).

(Equation 2)

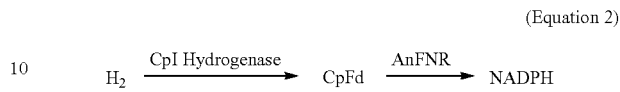

$$H_2 \xrightarrow{\text{CpI Hydrogenase}} CpFd \xrightarrow{\text{AnFNR}} NADPH$$

TABLE 1

Active FNR concentrations determined from the NADPH assay. Assay Results

| Sample | [Soluble Protein added] (nM) | NADPH Formation Rate (nmole µL$^{-1}$ min$^{-1}$) | [Active FNR] (nM) | % Active FNR |
|---|---|---|---|---|
| CpI | 7.30 | 0.05 | 1.12 | 15.3 |
| AnFNR | 2.07 | 0.18 | 3.68 | 177 |
| (GSA)$_5$ | 14.5 | 0.38 | 7.95 | 55.0 |
| (GSA)$_8$ | 12.8 | 0.60 | 12.4 | 97.3 |
| (GSA)$_{12}$ | 18.9 | ND | ND | ND |
| (GSA)$_{15}$ | 14.4 | 0.69 | 14.5 | 100.6 |

Previous CFPS reactions, where FAD was supplemented at 50 µM, have successfully produced active AnFNR. As shown in Table 1, the majority of the AnFNR produced as part of the fusion protein was active for (GSA)$_5$, (GSA)$_8$, and (GSA)$_{15}$. The assay measuring the activity of (GSA)$_{12}$ was inconclusive. Only a small background activity was observed for the CpI hydrogenase cell-free reaction product. The data presented in Table 1 indicate that the AnFNR portions of the (GSA)$_8$ and (GSA)$_{15}$ fusion proteins are close to fully active while the (GSA)$_5$ version appears to be approximately half active.

SDS-PAGE characterization was done, and an autoradiogram acquired in order to visualize the proteins produced by CFPS (see FIG. 5).

Finally, the fusion proteins were tested for their ability to produce hydrogen from NADPH. The following reagents were combined anaerobically (in a glove box with an atmosphere of 2% hydrogen and 98% nitrogen) in a 8.5 mL serum vial fitted with a small inner container: (1) 15 µL of the CFPS reaction product mixture, (2) 1.32 µL of 1140 µM CpFd (final concentration 50 µM), (3) 1.68 µL water, (4) 3.00 µL of 1M Tris (final concentration 100 mM), (5) 1.50 µL of glucose-6-phosphate dehydrogenase (G6PD) from yeast (Sigma-Aldrich G4134) to give a final concentration of 0.05 units/µL, (6) 1.50 µL of 10 mM glucose-6-phosphate (G6P, final concentration 5 mM). The G6PD and G6P constitute a NADPH regeneration system that functions to reduce NADP$^+$ to NADPH in order to maintain a constant concentration of NADPH and a low concentration of NADP$^+$. The vial was sealed with a septum and an aluminum crimp cap, removed from the anaerobic glovebox, purged with nitrogen for 5 minutes, placed in a 37° C. water bath for 5 minutes, re-purged for 5 minutes to remove any hydrogen produced from reduced species, replaced into the water bath, and the reaction initiated after thermal equilibration by the addition of 6.00 µL of 10 mM NADPH (final concentration 2 mM). The final volume of the reaction was 30 mL. The reaction preparation and initiation procedure is diagrammed in FIG. 6.

The hydrogen concentration in the headspace was periodically measured by removing 2004 of the headspace gas with a glass syringe and injecting into an Agilent 6890 GC-TCD gas chromatograph with a Restek Shincarbon column for hydrogen analysis. Hydrogen concentrations in the injected volume were determined from peak areas by comparing to calibration curves made from standards with known hydrogen concentrations. Results are presented in FIG. 7.

Figure 7:
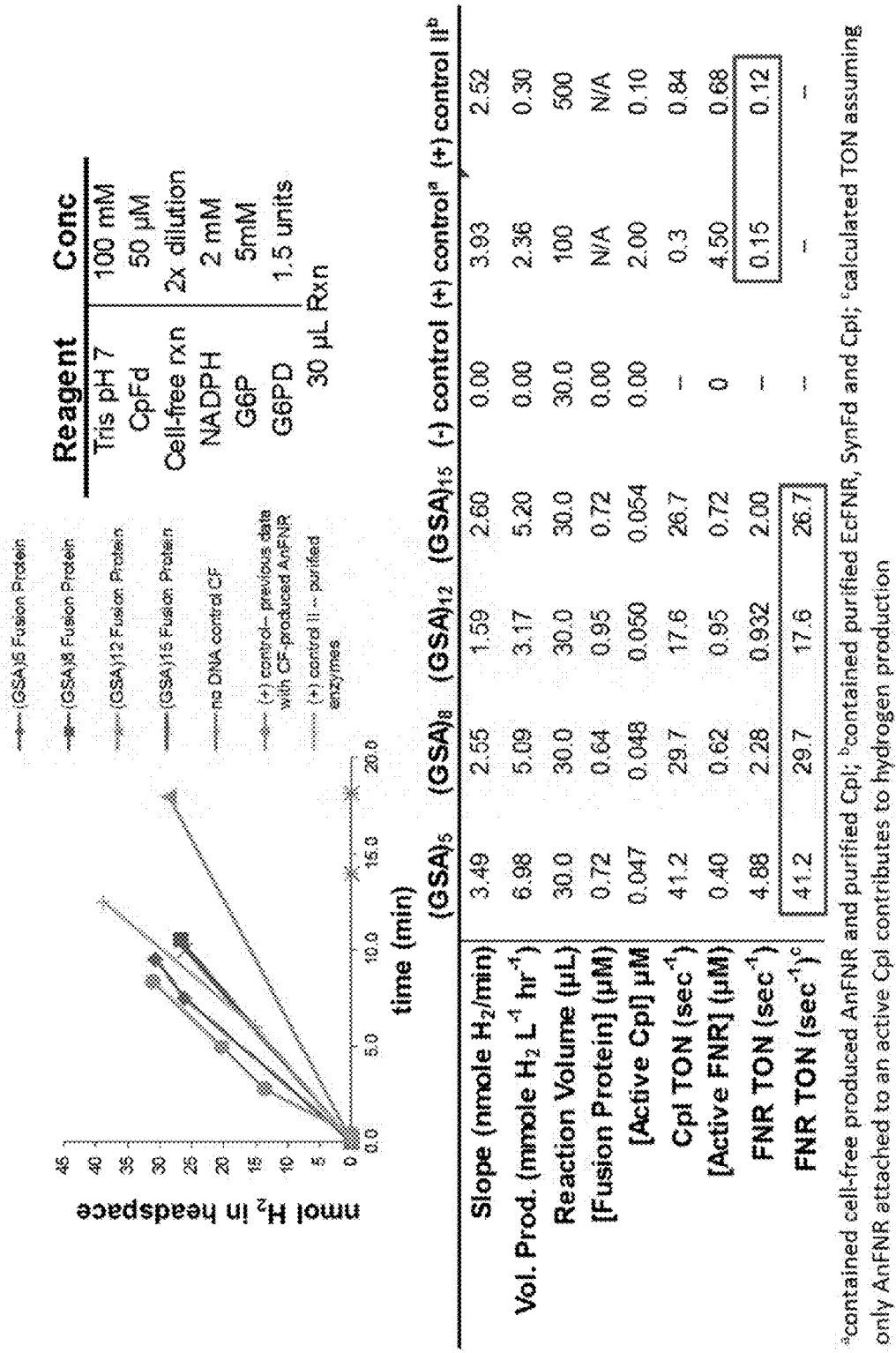
FIG. 7. Hydrogen Production from NADPH for the four fusion proteins, negative control (no DNA control CF), and two positive controls. TON denotes the enzyme turnover number (number of reactions catalyzed per second by a single enzyme molecule). Red boxes highlight the observed TONs for the FNR enzyme, believed to be rate-limiting in the pathway.

In FIG. 7, data for seven hydrogen production reactions are presented. The first four columns contain data from the four fusion proteins. The fifth, sixth, and seventh contain data from control reactions. The negative control hydrogen production reaction (column five) was done with the no DNA CFPS reaction; no hydrogen production was observed. Columns six and seven present data from two positive control reactions in which the FNR and CpI enzymes are not tethered to each other. The first positive control (column six) contained 4.5 μM cell-free-produced (unpurified) AnFNR and 2 μM purified CpI. The volumetric productivity of this reaction was 2.36 mmole $H_2$ $L^{-1}$ $hr^{-1}$. This reaction shows lower hydrogen production, on a volumetric basis, despite having 5-10 fold more AnFNR and 20 fold more active CpI, than the fusion protein-containing reactions. In the second positive control reaction (column seven), purified EcFNR, SynFd, and CpI, were used, at 0.68, 60, and 0.10 μM final concentrations, respectively. In this case, which more closely represents the concentration of the fusion proteins, the volumetric productivity is only 0.03 mmole $H_2$ $L^{-1}$ $hr^{-1}$. In both of these positive controls, the FNR TON is 0.12-0.15, which again is considerably lower than that observed for the fusion proteins.

Figure 8:
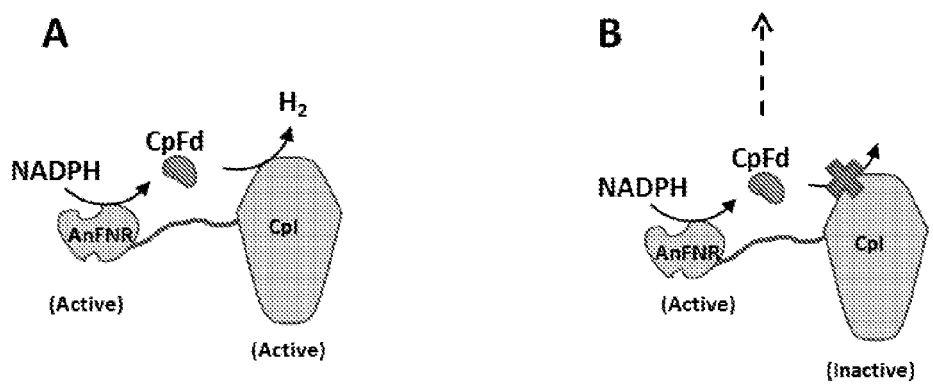
FIG. 8. Illustration of possible fusion protein reactions for hydrogen production from NADPH. Solid arrows indicate electron transfer through the indicated enzyme; dashed arrows indicate diffusion of the CpFd protein. (A) Both AnFNR and CpI are active and each reduced CpFd produced by AnFNR is oxidized by CpI to produce hydrogen. (B) Only AnFNR is active; the CpFd cannot be oxidized by the inactive CpI and diffuses away.

As shown in FIG. 7, the hydrogen volumetric productivities observed for the four fusion proteins were between 3 and 7 mmole $H_2$ $L^{-1}$ $hr^{-1}$. We have previously measured volumetric productivities with purified (non-fusion protein) proteins as high as 12 mmole $H_2$ L $hr^{-1}$, but only with AnFNR concentrations of 100 μM (we believe that the AnFNR is the limiting enzyme in this technology). The CpI and FNR TONs presented in FIG. 7 are the highest we have observed to date. Two methods can be used to determine the FNR TON—the first is to use the total concentration of active FNR in the system, as determined previously through spectrophotometric activity assays (see Table 1). Using the total active FNR gives TONs between 1 and 5 $sec^{-1}$ for the four fusion proteins. The second method calculates the TON by assuming that only the FNRs attached to active CpI hydrogenase proteins participate in the hydrogen production reaction (see FIG. 8). This is likely the case as the hydrogen production and TONs shown in positive control II, which is the control most representative of the concentrations of the fusion proteins, is negligible compared to that observed with the fusion proteins. In other words, ferredoxin that is reduced by the FNR connected to an inactive CpI hydrogenase cannot react further and must diffuse away; only those fusion proteins with both active FNR and active hydrogenase are able to produce hydrogen at the rates shown in FIG. 7. These calculated TONs are highlighted in the red box in FIG. 7 for the four fusion protein reactions. Thus, the tethering of the AnFNR and CpI enzymes significantly increase their effective reactivity.

These fusion proteins can be used in a synthetic enzyme pathway (see FIG. 9). This enzymatic pathway is an industrial-scale hydrogen production platform used to produce hydrogen from biomass components, in the form of depolymerized starches, cellulose, hemicellulose, and other polysaccharides. Cell extracts containing overexpressed proteins are utilized to process the sugars to hydrogen in a bioreactor; the hydrogen is removed via a purge stream. The reactor runs for a period of days before needing to be recharged with fresh lysate. The fusion proteins of the invention, with their greatly improved performance, can significantly improve the economics of this process by increasing the specific and volumetric productivities.

What is claimed is:

1. A fusion protein comprising an active FeFe hydrogenase joined through a polypeptide linker to an active ferredoxin-NADP-reductase (FNR) in which the fusion protein, when provided in a cell lysate or a product of cell-free protein synthesis at a concentration of at least 0.64 µM is capable of catalyzing a volume production of $H_2$ of at least about 5 mmol $H_2$ $L^{-1}$ $hr^{-1}$ in a reaction mix comprising a sugar at a concentration of 5 mM and a ferredoxin at a concentration of 50 µM.

2. The fusion protein of claim 1, wherein the active hydrogenase has at least about 90% sequence identity to one of the following hydrogenases: Chlamydomonas reinhardtii ironiron-hydrogenase; Clostridium pasteurianum hydrogenase; Megasphaera elsdenii hydrogenase; and Desulfovibrio vulgaris hydrogenase.

3. The fusion protein of claim 1, wherein the active FeFe hydrogenase of the fusion protein has at least about 20% of the activity of the native protein from which it is obtained when measured in the reaction mix of claim 2.

4. A fusion protein comprising an active FeFe hydrogenase joined through a polypeptide linker to an active ferredoxin-NADP-reductase (FNR) in which the fusion protein, when provided in a cell lysate or a product of cell-free protein at a concentration of at least 0.64 μM synthesis is capable of catalyzing a volume production of $H_2$ of at least about 5 mmol $H_2$ $L^{-1}$ $hr^{-1}$ in a reaction mix comprising a sugar at a concentration of 5 mM and a ferredoxin at a concentration of 50 μM, wherein the FeFe hydrogenase is Clostridium pasteurianum hydrogenase.

5. The fusion protein of claim 4, wherein the linker is a flexible linker joined to the carboxy terminus of the FeFe hydrogenase and the amino terminus of the FNR.

6. The fusion protein of claim 5, wherein the linker is from 4 to 40 amino acids in length.

7. The fusion protein of claim 6, wherein the linker is comprised of glycine, alanine, leucine, serine, valine and threonine.

8. The fusion protein of claim 4, wherein the active Ferredoxin-NADP-reductase (FNR) of the fusion protein has at least about 50% of the activity of the native protein from which it is obtained when measured in the reaction mix of claim 5.

9. The fusion protein of claim 4, wherein the turnover number (TON) for the FNR domain of the fusion protein of the invention is at least about 10 $sec^{-1}$ when measured in the reaction mix of claim 5.

10. The fusion protein of claim 4, wherein the FNR is an active fragment of Anabaena variabilis FNR.

11. A fusion protein comprising an active FeFe hydrogenase joined through a polypeptide linker to an active ferredoxin-NADP-reductase (FNR) wherein the protein has an amino acid sequence set forth in any one of SEQ ID NO: 2, 4, 6, and 8.

12. A cell lysate comprising a fusion protein of claim 11.

13. A cell free protein synthesis reaction, comprising a fusion protein of claim 11.

* * * * *

SEQUENCE LISTING

```
<160> NUMBER OF SEQ ID NOS: 13

<210> SEQ ID NO 1
<211> LENGTH: 2682
<212> TYPE: DNA
<213> ORGANISM: Artificial Sequence
<220> FEATURE:
<223> OTHER INFORMATION: Synthetic nucleic acid sequence

<400> SEQUENCE: 1
atgaaaacga ttatcatcaa tggtgtacag tttaataccg atgaagacac tactatcctg      60
aaatttgcac gcgacaacaa tattgatatc tccgcactgt gttttctgaa taattgtaat     120
aatgacatca ataagtgtga aatctgtacc gtagaagtag agggtactgg cctggtaacc     180
gcctgtgata ccctgattga ggatggtatg attatcaaca ccaattccga tgctgtcaac     240
gaaaaaatca aatctcgcat ctctcaactg ctggacatcc atgaattcaa atgtggtcct     300
tgcaatcgtc gtgaaaactg tgaattcctg aaactggtta tcaaatataa agcacgtgct     360
tctaaaccat ttctgcctaa agataagact gaatatgtag atgaacgtag caaatccctg     420
actgtagatc gtaccaaatg cctgctgtgt ggccgttgtg ttaatgcctg tggcaaaaat     480
actgaaacct atgcaatgaa atttctgaac aaaaacggca aaaccatcat tggcgcagag     540
gatgaaaaat gcttcgatga caccaattgt ctgctgtgtg gtcaatgtat catcgcctgt     600
ccagtagcag cactgtccga aaaatcccac atggatcgcg taaaaaatgc cctgaatgcc     660
cctgaaaaac atgtaatcgt agctatggct ccatctgtcc gtgcttctat cggcgaactg     720
```

```
tttaacatgg gctttggcgt tgacgtaacc ggcaaaattt atactgctct gcgtcagctt    780
ggcttcgaca aaatcttcga catcaacttc ggcgcagata tgaccattat ggaagaggct    840
accgaactgg ttcaacgtat cgagaataat ggcccttttcc caatgtttac ctcttgctgc   900
ccaggttggg tacgtcaagc tgaaaattat tatcctgaac tgctgaataa tctttcctcc    960
gctaaatccc ctcaacagat ctttggtacc gctagcaaaa cttattatcc ttctatctct   1020
ggtcttgacc caaagaatgt atttactgta accgttatgc cgtgtacttc caaaaaattt   1080
gaagcagatc gtccacaaat ggaaaaagac ggcctgcgtg atatcgatgc tgttatcact   1140
actcgcgaac tggcaaaaat gattaaagat gctaaaatcc catttgctaa acttgaagat   1200
agcgaagcag accctgctat gggcgaatac agcggtgctg gtgccatctt tggtgcaact   1260
ggcggcgtta tggaagcagc tctgcgtagc gcaaaagact ttgctgaaaa cgctgaactt   1320
gaagatatcg aatataagca agttcgcggc ctgaatggta tcaagaagc ggaagtagaa    1380 atcaataaca caaatataaa cgtagctgtt atcaatggtg cttccaatct gtttaagttc   1440
atgaaatccg gcatgattaa cgaaaaacaa tatcatttca tcgaagtaat ggcttgtcat   1500
ggcggctgtg taaatggtgg tggccagcct catgtaaacc caaaagacct ggaaaaagtg   1560
gacatcaaaa aagtacgtgc ttctgtactg tataatcagg atgaacatct ttccaagcgc   1620
aaatctcatg aaaataccgc actggttaaa atgtatcaga actatttcgg caaaccaggt   1680
gaaggtcgtg cccatgaaat cctgcacttt aaatataaaa aaggctctgc tggtagtgcc   1740
ggctcggcag ttcagctgg tagtgccacc caggcgaaag cgaaacatgc agatgtcccg    1800
gtgaatctgt atcgtccaaa tgcgccgttt attggcaagg tgattagcaa tgaaccgctg   1860 gtgaagaag gcggcattgg cattgtgcag catatcaagt ttgatttaac cggcggtaat    1920
ctgaagtata tagaaggcca gagcattgga attattcctc cgggcgtgga taagaacggc   1980
aaaccggaaa aactgcggtt gtatagcatt gcgagcaccc gtcatggcga tgacgtggat   2040
gataaaacca tatccctgtg cgtgcgtcag ctggaatata agcatcctga atcagggaa    2100 accgtgtatg gggtttgcag cacctatctg acccatattg aaccgggcag cgaagtgaaa   2160
atcaccggcc cagtgggcaa agaaatgctg ttgcccgatg atcccgaagc gaatgtcatc   2220
atgctggcga ccggcaccgg catagcaccg atgcgtacct acttatggcg tatgtttaaa   2280
gatgcagaac gtgcggcgaa tccggagtac cagtttaagg gctttagctg gctggtgttc   2340
ggcgtgccaa ccacccccaa catcctgtat aaagaggaac tggaagaaat tcagcagaaa   2400
tacccggata actttcgttt gacctatgcg attagccgtg aacagaaaaa tccgcagggc   2460
ggtcgtatgt atattcaaga tcgtgtggcg gaacatgcgg atgaactttg gcagctgatt   2520
aagaatcaaa aacccataac ctatatttgc ggcctgcgtg gcatggaaga gggcattgat   2580
gcggcgctga gcgcagccgc agcaaaagag ggtgtgacct ggagcgatta tcagaaagat   2640
ctgaaaaaag ccggacgttg gcatgtggaa acctattaat aa                     2682
```

<210> SEQ ID NO 2
<211> LENGTH: 892
<212> TYPE: PRT
<213> ORGANISM: Artificial Sequence
<220> FEATURE:
<223> OTHER INFORMATION: Synthetic amino acid sequence

<400> SEQUENCE: 2

Met Lys Thr Ile Ile Ile Asn Gly Val Gln Phe Asn Thr Asp Glu Asp
1               5                   10                  15

```
Thr Thr Ile Leu Lys Phe Ala Arg Asp Asn Ile Asp Ile Ser Ala
             20                  25                  30

Leu Cys Phe Leu Asn Asn Cys Asn Asn Asp Ile Asn Lys Cys Glu Ile
             35                  40                  45

Cys Thr Val Glu Val Glu Gly Thr Gly Leu Val Thr Ala Cys Asp Thr
 50                  55                  60

Leu Ile Glu Asp Gly Met Ile Ile Asn Thr Asn Ser Asp Ala Val Asn
 65                  70                  75                  80

Glu Lys Ile Lys Ser Arg Ile Ser Gln Leu Leu Asp Ile His Glu Phe
                 85                  90                  95

Lys Cys Gly Pro Cys Asn Arg Arg Glu Asn Cys Glu Phe Leu Lys Leu
             100                 105                 110

Val Ile Lys Tyr Lys Ala Arg Ala Ser Lys Pro Phe Leu Pro Lys Asp
             115                 120                 125

Lys Thr Glu Tyr Val Asp Glu Arg Ser Lys Ser Leu Thr Val Asp Arg
 130                 135                 140

Thr Lys Cys Leu Leu Cys Gly Arg Cys Val Asn Ala Cys Gly Lys Asn
145                 150                 155                 160

Thr Glu Thr Tyr Ala Met Lys Phe Leu Asn Lys Asn Gly Lys Thr Ile
                 165                 170                 175

Ile Gly Ala Glu Asp Glu Lys Cys Phe Asp Asp Thr Asn Cys Leu Leu
             180                 185                 190

Cys Gly Gln Cys Ile Ile Ala Cys Pro Val Ala Ala Leu Ser Glu Lys
             195                 200                 205

Ser His Met Asp Arg Val Lys Asn Ala Leu Asn Ala Pro Glu Lys His
     210                 215                 220

Val Ile Val Ala Met Ala Pro Ser Val Arg Ala Ser Ile Gly Glu Leu
225                 230                 235                 240

Phe Asn Met Gly Phe Gly Val Asp Val Thr Gly Lys Ile Tyr Thr Ala
                 245                 250                 255

Leu Arg Gln Leu Gly Phe Asp Lys Ile Phe Asp Ile Asn Phe Gly Ala
             260                 265                 270

Asp Met Thr Ile Met Glu Glu Ala Thr Glu Leu Val Gln Arg Ile Glu
             275                 280                 285

Asn Asn Gly Pro Phe Pro Met Phe Thr Ser Cys Cys Pro Gly Trp Val
             290                 295                 300

Arg Gln Ala Glu Asn Tyr Tyr Pro Glu Leu Leu Asn Asn Leu Ser Ser
305                 310                 315                 320

Ala Lys Ser Pro Gln Gln Ile Phe Gly Thr Ala Ser Lys Thr Tyr Tyr
             325                 330                 335

Pro Ser Ile Ser Gly Leu Asp Pro Lys Asn Val Phe Thr Val Thr Val
             340                 345                 350

Met Pro Cys Thr Ser Lys Lys Phe Glu Ala Asp Arg Pro Gln Met Glu
             355                 360                 365

Lys Asp Gly Leu Arg Asp Ile Asp Ala Val Ile Thr Thr Arg Glu Leu
             370                 375                 380

Ala Lys Met Ile Lys Asp Ala Lys Ile Pro Phe Ala Lys Leu Glu Asp
385                 390                 395                 400

Ser Glu Ala Asp Pro Ala Met Gly Glu Tyr Ser Gly Ala Gly Ala Ile
                 405                 410                 415

Phe Gly Ala Thr Gly Gly Val Met Glu Ala Ala Leu Arg Ser Ala Lys
             420                 425                 430
```

```
Asp Phe Ala Glu Asn Ala Glu Leu Glu Asp Ile Glu Tyr Lys Gln Val
            435                 440                 445

Arg Gly Leu Asn Gly Ile Lys Glu Ala Glu Val Glu Ile Asn Asn Asn
450                 455                 460

Lys Tyr Asn Val Ala Val Ile Asn Gly Ala Ser Asn Leu Phe Lys Phe
465                 470                 475                 480

Met Lys Ser Gly Met Ile Asn Glu Lys Gln Tyr His Phe Ile Glu Val
            485                 490                 495

Met Ala Cys His Gly Gly Cys Val Asn Gly Gly Gln Pro His Val
            500                 505                 510

Asn Pro Lys Asp Leu Glu Lys Val Asp Ile Lys Lys Val Arg Ala Ser
            515                 520                 525

Val Leu Tyr Asn Gln Asp Glu His Leu Ser Lys Arg Lys Ser His Glu
    530                 535                 540

Asn Thr Ala Leu Val Lys Met Tyr Gln Asn Tyr Phe Gly Lys Pro Gly
545                 550                 555                 560

Glu Gly Arg Ala His Glu Ile Leu His Phe Lys Tyr Lys Lys Gly Ser
                565                 570                 575

Ala Gly Ser Ala Gly Ser Ala Gly Ser Ala Gly Ser Ala Thr Gln Ala
            580                 585                 590

Lys Ala Lys His Ala Asp Val Pro Val Asn Leu Tyr Arg Pro Asn Ala
    595                 600                 605

Pro Phe Ile Gly Lys Val Ile Ser Asn Glu Pro Leu Val Lys Glu Gly
            610                 615                 620

Gly Ile Gly Ile Val Gln His Ile Lys Phe Asp Leu Thr Gly Gly Asn
625                 630                 635                 640

Leu Lys Tyr Ile Glu Gly Gln Ser Ile Gly Ile Ile Pro Pro Gly Val
                645                 650                 655

Asp Lys Asn Gly Lys Pro Glu Lys Leu Arg Leu Tyr Ser Ile Ala Ser
            660                 665                 670

Thr Arg His Gly Asp Asp Val Asp Asp Lys Thr Ile Ser Leu Cys Val
    675                 680                 685

Arg Gln Leu Glu Tyr Lys His Pro Glu Ser Gly Glu Thr Val Tyr Gly
690                 695                 700

Val Cys Ser Thr Tyr Leu Thr His Ile Glu Pro Gly Ser Glu Val Lys
705                 710                 715                 720

Ile Thr Gly Pro Val Gly Lys Glu Met Leu Leu Pro Asp Asp Pro Glu
                725                 730                 735

Ala Asn Val Ile Met Leu Ala Thr Gly Thr Gly Ile Ala Pro Met Arg
            740                 745                 750

Thr Tyr Leu Trp Arg Met Phe Lys Asp Ala Glu Arg Ala Ala Asn Pro
    755                 760                 765

Glu Tyr Gln Phe Lys Gly Phe Ser Trp Leu Val Phe Gly Val Pro Thr
770                 775                 780

Thr Pro Asn Ile Leu Tyr Lys Glu Glu Leu Glu Glu Ile Gln Gln Lys
785                 790                 795                 800

Tyr Pro Asp Asn Phe Arg Leu Thr Tyr Ala Ile Ser Arg Glu Gln Lys
                805                 810                 815

Asn Pro Gln Gly Gly Arg Met Tyr Ile Gln Asp Arg Val Ala Glu His
            820                 825                 830

Ala Asp Glu Leu Trp Gln Leu Ile Lys Asn Gln Lys Thr His Thr Tyr
    835                 840                 845

Ile Cys Gly Leu Arg Gly Met Glu Glu Gly Ile Asp Ala Ala Leu Ser
```

```
                    850                855                860
Ala Ala Ala Ala Lys Glu Gly Val Thr Trp Ser Asp Tyr Gln Lys Asp
865                 870                875                880

Leu Lys Lys Ala Gly Arg Trp His Val Glu Thr Tyr
                885                890

<210> SEQ ID NO 3
<211> LENGTH: 2709
<212> TYPE: DNA
<213> ORGANISM: Artificial Sequence
<220> FEATURE:
<223> OTHER INFORMATION: Synthetic nucleic acid sequence

<400> SEQUENCE: 3
atgaaaacga ttatcatcaa tggtgtacag tttaataccg atgaagacac tactatcctg      60
aaatttgcac gcgacaacaa tattgatatc tccgcactgt gttttctgaa taattgtaat     120
aatgacatca ataagtgtga atctgtaccg tagaagtag agggtactgg cctggtaacc      180
gcctgtgata ccctgattga ggatggtatg attatcaaca ccaattccga tgctgtcaac     240
gaaaaaatca aatctcgcat ctctcaactg ctggacatcc atgaattcaa atgtggtcct     300
tgcaatcgtc gtgaaaactg tgaattcctg aaactggtta tcaaatataa agcacgtgct     360
tctaaaccat ttctgcctaa agataagact gaatatgtag atgaacgtag caaatccctg     420
actgtagatc gtaccaaatg cctgctgtgt ggccgttgtg ttaatgcctg tgcaaaaat     480 actgaaacct atgcaatgaa atttctgaac aaaaacggca aaaccatcat ggcgcagag     540 gatgaaaaat gcttcgatga caccaattgt ctgctgtgtg gtcaatgtat catcgcctgt     600
ccagtagcag cactgtccga aaatcccac atggatcgcg taaaaatgc cctgaatgcc     660 cctgaaaaac atgtaatcgt agctatggct ccatctgtcc gtgcttctat cggcgaactg     720
tttaacatgg gctttggcgt tgacgtaacc ggcaaaattt atactgctct cgtcagctt     780 ggcttcgaca aaatcttcga catcaacttc ggcgcagata tgaccattat ggaagaggct     840
accgaactgg ttcaacgtat cgagaataat ggccccttcc caatgtttac ctcttgctgc     900
ccaggttggg tacgtcaagc tgaaaattat tatcctgaac tgctgaataa tctttcctcc     960
gctaaatccc ctcaacagat ctttggtacc gctagcaaaa cttattatcc ttctatctct    1020
ggtcttgacc caagaatgt atttactgta accgttatgc cgtgtacttc caaaaatt     1080 gaagcagatc gtccacaaat ggaaaaagac ggcctgcgtg atatcgatgc tgttatcact    1140
actcgcgaac tggcaaaaat gattaaagat gctaaaatcc catttgctaa acttgaagat    1200
agcgaagcag accctgctat gggcgaatac agcggtgctg gtgccatctt tggtgcaact    1260
ggcggcgtta tggaagcagc tctgcgtagc gcaaaagact tgctgaaaaa cgctgaactt    1320
gaagatatcg aatataagca agttcgcggc ctgaatggta tcaaagaagc ggaagtagaa    1380
atcaataaca caaatataaa cgtagctgtt atcaatggtg cttccaatct gtttaagttc    1440
atgaaatccg gcatgattaa cgaaaaacaa tatcatttca tcgaagtaat ggcttgtcat    1500
ggcggctgtg taaatggtgg tggccagcct catgtaaacc caaaagacct ggaaaaagtg    1560
gacatcaaaa agtacgtgc ttctgtactg tataatcagg atgaacatct ttccaagcgc    1620
aaatctcatg aaaataccgc actggttaaa atgtatcaga actatttcgg caaaccaggt    1680
gaaggtcgtg cccatgaaat cctgcacttt aaatataaaa aaggctctgc tggtagtgcc    1740
ggctcggcag gctccgcagg ttcagcgggc tcggcaggtt cagctggtag tgccacccag    1800
gcgaaagcga acatgcaga tgtcccggtg aatctgtatc gtccaaatgc gccgtttatt    1860
```

```
ggcaaggtga ttagcaatga accgctggtg aaagaaggcg gcattggcat tgtgcagcat    1920
atcaagtttg atttaaccgg cggtaatctg aagtatatag aaggccagag cattggaatt    1980
attcctccgg gcgtggataa gaacggcaaa ccggaaaaac tgcggttgta tagcattgcg    2040
agcacccgtc atggcgatga cgtggatgat aaaaccatat ccctgtgcgt gcgtcagctg    2100
gaatataagc atcctgaatc aggggaaacc gtgtatgggg tttgcagcac ctatctgacc    2160
catattgaac cggcagcga agtgaaaatc accggcccag tgggcaaaga aatgctgttg    2220
cccgatgatc ccgaagcgaa tgtcatcatg ctggcgaccg gcaccggcat agcaccgatg    2280
cgtacctact tatggcgtat gtttaaagat gcagaacgtg cggcgaatcc ggagtaccag    2340
tttaagggct ttagctggct ggtgttcggc gtgccaacca ccccaacat cctgtataaa     2400 gaggaactgg aagaaattca gcagaaatac ccggataact ttcgtttgac ctatgcgatt    2460
agccgtgaac agaaaaatcc gcagggcggt cgtatgtata ttcaagatcg tgtggcggaa    2520
catgcggatg aactttggca gctgattaag aatcaaaaaa cccataccta tatttgcggc    2580
ctgcgtggca tggaagaggg cattgatgcg cgctgagcg cagccgcagc aaaagagggt     2640
gtgacctgga gcgattatca gaaagatctg aaaaaagccg gacgttggca tgtggaaacc    2700
tattaataa                                                            2709

<210> SEQ ID NO 4
<211> LENGTH: 901
<212> TYPE: PRT
<213> ORGANISM: Artificial Sequence
<220> FEATURE:
<223> OTHER INFORMATION: Synthetic amino acid sequence

<400> SEQUENCE: 4

Met Lys Thr Ile Ile Ile Asn Gly Val Gln Phe Asn Thr Asp Glu Asp
1               5                   10                  15

Thr Thr Ile Leu Lys Phe Ala Arg Asp Asn Asn Ile Asp Ile Ser Ala
            20                  25                  30

Leu Cys Phe Leu Asn Asn Cys Asn Asn Asp Ile Asn Lys Cys Glu Ile
        35                  40                  45

Cys Thr Val Glu Val Glu Gly Thr Gly Leu Val Thr Ala Cys Asp Thr
    50                  55                  60

Leu Ile Glu Asp Gly Met Ile Ile Asn Thr Asn Ser Asp Ala Val Asn
65                  70                  75                  80

Glu Lys Ile Lys Ser Arg Ile Ser Gln Leu Leu Asp Ile His Glu Phe
                85                  90                  95

Lys Cys Gly Pro Cys Asn Arg Arg Glu Asn Cys Glu Phe Leu Lys Leu
            100                 105                 110

Val Ile Lys Tyr Lys Ala Arg Ala Ser Lys Pro Phe Leu Pro Lys Asp
        115                 120                 125

Lys Thr Glu Tyr Val Asp Glu Arg Ser Lys Ser Leu Thr Val Asp Arg
    130                 135                 140

Thr Lys Cys Leu Leu Cys Gly Arg Cys Val Asn Ala Cys Gly Lys Asn
145                 150                 155                 160

Thr Glu Thr Tyr Ala Met Lys Phe Leu Asn Lys Asn Gly Lys Thr Ile
                165                 170                 175

Ile Gly Ala Glu Asp Glu Lys Cys Phe Asp Asp Thr Asn Cys Leu Leu
            180                 185                 190

Cys Gly Gln Cys Ile Ile Ala Cys Pro Val Ala Ala Leu Ser Glu Lys
        195                 200                 205
```

-continued

Ser His Met Asp Arg Val Lys Asn Ala Leu Asn Ala Pro Glu Lys His
    210                 215                 220

Val Ile Val Ala Met Ala Pro Ser Val Arg Ala Ser Ile Gly Glu Leu
225                 230                 235                 240

Phe Asn Met Gly Phe Gly Val Asp Val Thr Gly Lys Ile Tyr Thr Ala
                245                 250                 255

Leu Arg Gln Leu Gly Phe Asp Lys Ile Phe Asp Ile Asn Phe Gly Ala
                260                 265                 270

Asp Met Thr Ile Met Glu Glu Ala Thr Glu Leu Val Gln Arg Ile Glu
            275                 280                 285

Asn Asn Gly Pro Phe Pro Met Phe Thr Ser Cys Cys Pro Gly Trp Val
    290                 295                 300

Arg Gln Ala Glu Asn Tyr Tyr Pro Glu Leu Leu Asn Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Leu Asp Pro Lys Asn Val Phe Thr Val Thr Val
                340                 345                 350

Met Pro Cys Thr Ser Lys Lys Phe Glu Ala Asp Arg Pro Gln Met Glu
            355                 360                 365

Lys Asp Gly Leu Arg Asp Ile Asp Ala Val Ile Thr Thr Arg Glu Leu
    370                 375                 380

Ala Lys Met Ile Lys Asp Ala Lys Ile Pro Phe Ala Lys Leu Glu Asp
385                 390                 395                 400

Ser Glu Ala Asp Pro Ala Met Gly Glu Tyr Ser Gly Ala Gly Ala Ile
                405                 410                 415

Phe Gly Ala Thr Gly Gly Val Met Glu Ala Ala Leu Arg Ser Ala Lys
                420                 425                 430

Asp Phe Ala Glu Asn Ala Glu Leu Gly Asp Ile Glu Tyr Lys Gln Val
            435                 440                 445

Arg Gly Leu Asn Gly Ile Lys Glu Ala Glu Val Glu Ile Asn Asn Asn
    450                 455                 460

Lys Tyr Asn Val Ala Val Ile Asn Gly Ala Ser Asn Leu Phe Lys Phe
465                 470                 475                 480

Met Lys Ser Gly Met Ile Asn Glu Lys Gln Tyr His Phe Ile Glu Val
                485                 490                 495

Met Ala Cys His Gly Gly Cys Val Asn Gly Gly Gln Pro His Val
            500                 505                 510

Asn Pro Lys Asp Leu Glu Lys Val Asp Ile Lys Lys Val Arg Ala Ser
    515                 520                 525

Val Leu Tyr Asn Gln Asp Glu His Leu Ser Lys Arg Lys Ser His Glu
530                 535                 540

Asn Thr Ala Leu Val Lys Met Tyr Gln Asn Tyr Phe Gly Lys Pro Gly
545                 550                 555                 560

Glu Gly Arg Ala His Glu Ile Leu His Phe Lys Tyr Lys Lys Gly Ser
                565                 570                 575

Ala Gly Ser Ala Gly Ser Ala Gly Ser Ala Gly Ser Ala
                580                 585                 590

Gly Ser Ala Gly Ser Ala Thr Gln Ala Lys Ala Lys His Ala Asp Val
            595                 600                 605

Pro Val Asn Leu Tyr Arg Pro Asn Ala Pro Phe Ile Gly Lys Val Ile
    610                 615                 620

```
Ser Asn Glu Pro Leu Val Lys Glu Gly Gly Ile Gly Ile Val Gln His
625                 630                 635                 640

Ile Lys Phe Asp Leu Thr Gly Gly Asn Leu Lys Tyr Ile Glu Gly Gln
            645                 650                 655

Ser Ile Gly Ile Ile Pro Pro Gly Val Asp Lys Asn Gly Lys Pro Glu
        660                 665                 670

Lys Leu Arg Leu Tyr Ser Ile Ala Ser Thr Arg His Gly Asp Asp Val
    675                 680                 685

Asp Asp Lys Thr Ile Ser Leu Cys Val Arg Gln Leu Glu Tyr Lys His
690                 695                 700

Pro Glu Ser Gly Glu Thr Val Tyr Gly Val Cys Ser Thr Tyr Leu Thr
705                 710                 715                 720

His Ile Glu Pro Gly Ser Glu Val Lys Ile Thr Gly Pro Val Gly Lys
            725                 730                 735

Glu Met Leu Leu Pro Asp Asp Pro Glu Ala Asn Val Ile Met Leu Ala
        740                 745                 750

Thr Gly Thr Gly Ile Ala Pro Met Arg Thr Tyr Leu Trp Arg Met Phe
    755                 760                 765

Lys Asp Ala Glu Arg Ala Ala Asn Pro Glu Tyr Gln Phe Lys Gly Phe
770                 775                 780

Ser Trp Leu Val Phe Gly Val Pro Thr Thr Pro Asn Ile Leu Tyr Lys
785                 790                 795                 800

Glu Glu Leu Glu Glu Ile Gln Gln Lys Tyr Pro Asp Asn Phe Arg Leu
            805                 810                 815

Thr Tyr Ala Ile Ser Arg Glu Gln Lys Asn Pro Gln Gly Gly Arg Met
        820                 825                 830

Tyr Ile Gln Asp Arg Val Ala Glu His Ala Asp Glu Leu Trp Gln Leu
    835                 840                 845

Ile Lys Asn Gln Lys Thr His Thr Tyr Ile Cys Gly Leu Arg Gly Met
850                 855                 860

Glu Glu Gly Ile Asp Ala Ala Leu Ser Ala Ala Ala Lys Glu Gly
865                 870                 875                 880

Val Thr Trp Ser Asp Tyr Gln Lys Asp Leu Lys Lys Ala Gly Arg Trp
            885                 890                 895

His Val Glu Thr Tyr
            900

<210> SEQ ID NO 5
<211> LENGTH: 2745
<212> TYPE: DNA
<213> ORGANISM: Artificial Sequence
<220> FEATURE:
<223> OTHER INFORMATION: Synthetic nucleic acid sequence

<400> SEQUENCE: 5
atgaaaacga ttatcatcaa tggtgtacag tttaataccg atgaagacac tactatcctg      60
aaatttgcac gcgacaacaa tattgatatc tccgcactgt gttttctgaa taattgtaat     120
aatgacatca ataagtgtga atctgtaccg gtagaagtag agggtactgg cctggtaacc     180
gcctgtgata ccctgattga ggatggtatg attatcaaca ccaattccga tgctgtcaac     240
gaaaaaatca atctcgcat ctctcaactg ctggacatcc atgaattcaa atgtggtcct     300
tgcaatcgtc gtgaaaactg tgaattcctg aaactggtta tcaaatataa agcacgtgct     360
tctaaaccat ttctgcctaa agataagact gaatatgtag atgaacgtag caaatccctg     420
actgtagatc gtaccaaatg cctgctgtgt ggccgttgtg ttaatgcctg tggcaaaaat     480
```

```
actgaaacct atgcaatgaa atttctgaac aaaaacggca aaaccatcat tggcgcagag    540
gatgaaaaat gcttcgatga caccaattgt ctgctgtgtg gtcaatgtat catcgcctgt    600
ccagtagcag cactgtccga aaatcccac atggatcgcg taaaaaatgc cctgaatgcc     660
cctgaaaaac atgtaatcgt agctatggct ccatctgtcc gtgcttctat cggcgaactg    720
tttaacatgg gctttggcgt tgacgtaacc ggcaaaattt atactgctct gcgtcagctt    780
ggcttcgaca aaatcttcga catcaacttc ggcgcagata tgaccattat ggaagaggct    840
accgaactgg ttcaacgtat cgagaataat ggccctttcc caatgtttac ctcttgctgc    900
ccaggttggg tacgtcaagc tgaaaattat tatcctgaac tgctgaataa tctttcctcc    960
gctaaatccc ctcaacagat ctttggtacc gctagcaaaa cttattatcc ttctatctct    1020
ggtcttgacc caaagaatgt atttactgta accgttatgc cgtgtacttc caaaaaattt    1080
gaagcagatc gtccacaaat ggaaaagac ggcctgcgtg atatcgatgc tgttatcact     1140
actcgcgaac tggcaaaaat gattaaagat gctaaaatcc catttgctaa acttgaagat    1200
agcgaagcag accctgctat gggcgaatac agcggtgctg gtgccatctt tggtgcaact    1260
ggcggcgtta tggaagcagc tctgcgtagc gcaaaagact ttgctgaaaa cgctgaactt    1320
gaagatatcg aatataagca agttcgcggc ctgaatggta tcaaagaagc ggaagtagaa    1380
atcaataaca acaaatataa cgtagctgtt atcaatggtg cttccaatct gtttaagttc    1440
atgaaatccg gcatgattaa cgaaaaacaa tatcatttca tcgaagtaat ggcttgtcat    1500
ggcggctgtg taaatggtgg tggccagcct catgtaaacc caaaagacct ggaaaaagtg    1560
gacatcaaaa aagtacgtgc ttctgtactg tataatcagg atgaacatct ttccaagcgc    1620
aaatctcatg aaaataccgc actggttaaa atgtatcaga actatttcgg caaaccaggt    1680
gaaggtcgtg cccatgaaat cctgcacttt aaatataaaa aaggctctgc tggtagtgcc    1740
ggctcggcag gctccgcagg ctcggcgggt agcgccggca gtgccggttc cgcaggttca    1800
gcgggctcgg caggttcagc tggtagtgcc acccaggcga aagcgaaaca tgcagatgtc    1860
ccggtgaatc tgtatcgtcc aaatgcgccg tttattggca aggtgattag caatgaaccg    1920
ctggtgaaag aaggcggcat tggcattgtg cagcatatca gtttgatttt aaccggcggt    1980
aatctgaagt atatagaagg ccagagcatt ggaattattc ctccgggcgt ggataagaac    2040
ggcaaaccgg aaaaactgcg gttgtatagc attgcgagca cccgtcatgg cgatgacgtg    2100
gatgataaaa ccatatccct gtgcgtgcgt cagctggaat ataagcatcc tgaatcaggg    2160
gaaaccgtgt atgggtttg cagcacctat ctgacccata ttgaaccggg cagcgaagtg    2220
aaaatcaccg gcccagtggg caaagaaatg ctgttgcccg atgatcccga agcgaatgtc    2280
atcatgctgg cgaccggcac cggcatagca ccgatgcgta cctacttatg gcgtatgttt    2340
aaagatgcag aacgtgcggc gaatccggag taccagttta agggctttag ctggctggtg    2400
ttcggcgtgc aaccaccccc caacatcctg tataaagagg aactggaaga aattcagcag    2460
aaatacccgg ataactttcg tttgacctat gcgattagcc gtgaacagaa aaatccgcag    2520
ggcggtcgta tgtatattca agatcgtgtg gcggaacatg cggatgaact ttggcagctg    2580
attaagaatc aaaaaaccca tacctatatt tgcggcctgc gtggcatgga agagggcatt    2640
gatgcggcgc tgagcgcagc cgcagcaaaa gagggtgtga cctggagcga ttatcagaaa    2700
gatctgaaaa aagccggacg ttggcatgtg gaaacctatt aataa                    2745
```

<210> SEQ ID NO 6

<211> LENGTH: 913
<212> TYPE: PRT
<213> ORGANISM: Artificial Sequence
<220> FEATURE:
<223> OTHER INFORMATION: Synthetic amino acid sequence

<400> SEQUENCE: 6

```
Met Lys Thr Ile Ile Ile Asn Gly Val Gln Phe Asn Thr Asp Glu Asp
1               5                   10                  15

Thr Thr Ile Leu Lys Phe Ala Arg Asp Asn Asn Ile Asp Ile Ser Ala
            20                  25                  30

Leu Cys Phe Leu Asn Asn Cys Asn Asn Asp Ile Asn Lys Cys Glu Ile
        35                  40                  45

Cys Thr Val Glu Val Glu Gly Thr Gly Leu Val Thr Ala Cys Asp Thr
    50                  55                  60

Leu Ile Glu Asp Gly Met Ile Ile Asn Thr Asn Ser Asp Ala Val Asn
65                  70                  75                  80

Glu Lys Ile Lys Ser Arg Ile Ser Gln Leu Leu Asp Ile His Glu Phe
                85                  90                  95

Lys Cys Gly Pro Cys Asn Arg Arg Glu Asn Cys Glu Phe Leu Lys Leu
            100                 105                 110

Val Ile Lys Tyr Lys Ala Arg Ala Ser Lys Pro Phe Leu Pro Lys Asp
        115                 120                 125

Lys Thr Glu Tyr Val Asp Glu Arg Ser Lys Ser Leu Thr Val Asp Arg
    130                 135                 140

Thr Lys Cys Leu Leu Cys Gly Arg Cys Val Asn Ala Cys Gly Lys Asn
145                 150                 155                 160

Thr Glu Thr Tyr Ala Met Lys Phe Leu Asn Lys Asn Gly Lys Thr Ile
                165                 170                 175

Ile Gly Ala Glu Asp Glu Lys Cys Phe Asp Asp Thr Asn Cys Leu Leu
            180                 185                 190

Cys Gly Gln Cys Ile Ile Ala Cys Pro Val Ala Ala Leu Ser Glu Lys
        195                 200                 205

Ser His Met Asp Arg Val Lys Asn Ala Leu Asn Ala Pro Glu Lys His
    210                 215                 220

Val Ile Val Ala Met Ala Pro Ser Val Arg Ala Ser Ile Gly Glu Leu
225                 230                 235                 240

Phe Asn Met Gly Phe Gly Val Asp Val Thr Gly Lys Ile Tyr Thr Ala
                245                 250                 255

Leu Arg Gln Leu Gly Phe Asp Lys Ile Phe Asp Ile Asn Phe Gly Ala
            260                 265                 270

Asp Met Thr Ile Met Glu Glu Ala Thr Glu Leu Val Gln Arg Ile Glu
        275                 280                 285

Asn Asn Gly Pro Phe Pro Met Phe Thr Ser Cys Cys Pro Gly Trp Val
    290                 295                 300

Arg Gln Ala Glu Asn Tyr Tyr Pro Glu Leu Leu Asn Asn Leu Ser Ser
305                 310                 315                 320

Ala Lys Ser Pro Gln Gln Ile Phe Gly Thr Ala Ser Lys Thr Tyr Tyr
                325                 330                 335

Pro Ser Ile Ser Gly Leu Asp Pro Lys Asn Val Phe Thr Val Thr Val
            340                 345                 350

Met Pro Cys Thr Ser Lys Lys Phe Glu Ala Asp Arg Pro Gln Met Glu
        355                 360                 365

Lys Asp Gly Leu Arg Asp Ile Asp Ala Val Ile Thr Thr Arg Glu Leu
    370                 375                 380
```

```
Ala Lys Met Ile Lys Asp Ala Lys Ile Pro Phe Ala Lys Leu Glu Asp
385                 390                 395                 400

Ser Glu Ala Asp Pro Ala Met Gly Glu Tyr Ser Gly Ala Gly Ala Ile
            405                 410                 415

Phe Gly Ala Thr Gly Gly Val Met Glu Ala Ala Leu Arg Ser Ala Lys
            420                 425                 430

Asp Phe Ala Glu Asn Ala Glu Leu Glu Asp Ile Glu Tyr Lys Gln Val
        435                 440                 445

Arg Gly Leu Asn Gly Ile Lys Glu Ala Glu Val Glu Ile Asn Asn Asn
    450                 455                 460

Lys Tyr Asn Val Ala Val Ile Asn Gly Ala Ser Asn Leu Phe Lys Phe
465                 470                 475                 480

Met Lys Ser Gly Met Ile Asn Glu Lys Gln Tyr His Phe Ile Glu Val
            485                 490                 495

Met Ala Cys His Gly Cys Val Asn Gly Gly Gln Pro His Val
        500                 505                 510

Asn Pro Lys Asp Leu Glu Lys Val Asp Ile Lys Lys Val Arg Ala Ser
        515                 520                 525

Val Leu Tyr Asn Gln Asp Glu His Leu Ser Lys Arg Lys Ser His Glu
    530                 535                 540

Asn Thr Ala Leu Val Lys Met Tyr Gln Asn Tyr Phe Gly Lys Pro Gly
545                 550                 555                 560

Glu Gly Arg Ala His Glu Ile Leu His Phe Lys Tyr Lys Lys Gly Ser
            565                 570                 575

Ala Gly Ser Ala Gly Ser Ala Gly Ser Ala Gly Ser Ala
        580                 585                 590

Gly Ser Ala Gly Ser Ala Gly Ser Ala Gly Ser Ala Gly
    595                 600                 605

Ser Ala Thr Gln Ala Lys Ala Lys His Ala Asp Val Pro Val Asn Leu
    610                 615                 620

Tyr Arg Pro Asn Ala Pro Phe Ile Gly Lys Val Ile Ser Asn Glu Pro
625                 630                 635                 640

Leu Val Lys Glu Gly Ile Gly Ile Val Gln His Ile Lys Phe Asp
            645                 650                 655

Leu Thr Gly Gly Asn Leu Lys Tyr Ile Glu Gly Gln Ser Ile Gly Ile
            660                 665                 670

Ile Pro Pro Gly Val Asp Lys Asn Gly Lys Pro Glu Lys Leu Arg Leu
        675                 680                 685

Tyr Ser Ile Ala Ser Thr Arg His Gly Asp Asp Val Asp Asp Lys Thr
    690                 695                 700

Ile Ser Leu Cys Val Arg Gln Leu Glu Tyr Lys His Pro Glu Ser Gly
705                 710                 715                 720

Glu Thr Val Tyr Gly Val Cys Ser Thr Tyr Leu Thr His Ile Glu Pro
            725                 730                 735

Gly Ser Glu Val Lys Ile Thr Gly Pro Val Gly Lys Glu Met Leu Leu
            740                 745                 750

Pro Asp Asp Pro Glu Ala Asn Val Ile Met Leu Ala Thr Gly Thr Gly
        755                 760                 765

Ile Ala Pro Met Arg Thr Tyr Leu Trp Arg Met Phe Lys Asp Ala Glu
        770                 775                 780

Arg Ala Ala Asn Pro Glu Tyr Gln Phe Lys Gly Phe Ser Trp Leu Val
785                 790                 795                 800
```

Phe Gly Val Pro Thr Thr Pro Asn Ile Leu Tyr Lys Glu Glu Leu Glu
                    805                 810                 815

Glu Ile Gln Gln Lys Tyr Pro Asp Asn Phe Arg Leu Thr Tyr Ala Ile
                820                 825                 830

Ser Arg Glu Gln Lys Asn Pro Gln Gly Gly Arg Met Tyr Ile Gln Asp
            835                 840                 845

Arg Val Ala Glu His Ala Asp Glu Leu Trp Gln Leu Ile Lys Asn Gln
        850                 855                 860

Lys Thr His Thr Tyr Ile Cys Gly Leu Arg Gly Met Glu Glu Gly Ile
865                 870                 875                 880

Asp Ala Ala Leu Ser Ala Ala Ala Lys Glu Gly Val Thr Trp Ser
                    885                 890                 895

Asp Tyr Gln Lys Asp Leu Lys Lys Ala Gly Arg Trp His Val Glu Thr
                900                 905                 910

Tyr

<210> SEQ ID NO 7
<211> LENGTH: 2772
<212> TYPE: DNA
<213> ORGANISM: Artificial Sequence
<220> FEATURE:
<223> OTHER INFORMATION: Synthetic nucleic acid sequence

<400> SEQUENCE: 7

| | |
|---|---:|
| atgaaaacga ttatcatcaa tggtgtacag tttaataccg atgaagacac tactatcctg | 60 |
| aaatttgcac gcgacaacaa tattgatatc tccgcactgt gttttctgaa taattgtaat | 120 |
| aatgacatca ataagtgtga atctgtaccg tagaagtag agggtactgg cctggtaacc | 180 |
| gcctgtgata ccctgattga ggatggtatg attatcaaca ccaattccga tgctgtcaac | 240 |
| gaaaaaatca atctcgcat ctctcaactg ctggacatcc atgaattcaa atgtggtcct | 300 |
| tgcaatcgtc gtgaaaactg tgaattcctg aaactggtta tcaaatataa agcacgtgct | 360 |
| tctaaaccat ttctgcctaa agataagact gaatatgtag atgaacgtag caaatccctg | 420 |
| actgtagatc gtaccaaatg cctgctgtgt ggccgttgtg ttaatgcctg tggcaaaaat | 480 |
| actgaaacct atgcaatgaa atttctgaac aaaaacggca aaccatcat ggcgcagag | 540 |
| gatgaaaaat gcttcgatga caccaattgt ctgctgtgtg gtcaatgtat catcgcctgt | 600 |
| ccagtagcag cactgtccga aaatcccac atggatcgcg taaaaatgc cctgaatgcc | 660 |
| cctgaaaaac atgtaatcgt agctatggct ccatctgtcc gtgcttctat cggcgaactg | 720 |
| tttaacatgg gctttggcgt tgacgtaacc ggcaaaattt atactgctct gcgtcagctt | 780 |
| ggcttcgaca aaatcttcga catcaacttc ggcgcagata tgaccattat ggaagaggct | 840 |
| accgaactgg ttcaacgtat cgagaataat ggccctttcc caatgtttac ctcttgctgc | 900 |
| ccaggttggg tacgtcaagc tgaaattat tatcctgaac tgctgaataa tctttcctcc | 960 |
| gctaaatccc ctcaacagat ctttggtacc gctagcaaaa cttattatcc ttctatctct | 1020 |
| ggtcttgacc caagaatgt atttactgta accgttatgc cgtgtacttc caaaaaattt | 1080 |
| gaagcagatc gtccacaaat ggaaaaagac ggcctgcgtg atatcgatgc tgttatcact | 1140 |
| actcgcgaac tggcaaaaat gattaaagat gctaaaatcc catttgctaa acttgaagat | 1200 |
| agcgaagcag accctgctat gggcgaatac agcggtgctg gtgccatctt tggtgcaact | 1260 |
| ggcggcgtta tggaagcagc tctgcgtagc gcaaaagact ttgctgaaaa cgctgaactt | 1320 |
| gaagatatcg aatataagca agttcgcggc ctgaatggta tcaaagaagc ggaagtagaa | 1380 |

```
atcaataaca acaaatataa cgtagctgtt atcaatggtg cttccaatct gtttaagttc    1440
atgaaatccg gcatgattaa cgaaaaacaa tatcatttca tcgaagtaat ggcttgtcat    1500
ggcggctgtg taaatggtgg tggccagcct catgtaaacc caaagacct ggaaaaagtg    1560 gacatcaaaa aagtacgtgc ttctgtactg tataatcagg atgaacatct ttccaagcgc    1620
aaatctcatg aaaataccgc actggttaaa atgtatcaga actatttcgg caaaccaggt    1680
gaaggtcgtg cccatgaaat cctgcacttt aaatataaaa aaggctctgc tggtagtgcc    1740
ggctcggcag gctccgcagg ctcggcgggc tcagctggtt cagcgggttc cgccggtagc    1800
gccggcagtg ccggttccgc aggttcagcg ggctcggcag gttcagctgg tagtgccacc    1860
caggcgaaag cgaaacatgc agatgtcccg gtgaatctgt atcgtccaaa tgcgccgttt    1920
attggcaagg tgattagcaa tgaaccgctg gtgaaagaag gcggcattgg cattgtgcag    1980
catatcaagt ttgatttaac cggcggtaat ctgaagtata tagaaggcca gagcattgga    2040
attattcctc cgggcgtgga taagaacggc aaaccggaaa actgcggtt gtatagcatt    2100 gcgagcaccc gtcatggcga tgacgtggat gataaaacca tccctgtg cgtgcgtcag    2160 ctggaatata agcatcctga atcaggggaa accgtgtatg gggtttgcag cacctatctg    2220
acccatattg aaccgggcag cgaagtgaaa atcaccggcc cagtgggcaa agaaatgctg    2280
ttgcccgatg atcccgaagc gaatgtcatc atgctggcga ccggcaccgg catagcaccg    2340
atgcgtacct acttatggcg tatgtttaaa gatgcagaac gtgcggcgaa tccggagtac    2400
cagtttaagg gctttagctg gctggtgttc ggcgtgccaa ccaccccaa catcctgtat    2460 aaagaggaac tggaagaaat tcagcagaaa tacccggata actttcgttt gacctatgcg    2520
attagccgtg aacagaaaaa tccgcagggc ggtcgtatgt atattcaaga tcgtgtggcg    2580
gaacatgcgg atgaactttg gcagctgatt aagaatcaaa aaacccatac ctatatttgc    2640
ggcctgcgtg gcatggaaga gggcattgat gcggcgctga gcgcagccgc agcaaaagag    2700
ggtgtgacct ggagcgatta tcagaaagat ctgaaaaaag ccggacgttg gcatgtggaa    2760
acctattaat aa                                                       2772
```

<210> SEQ ID NO 8
<211> LENGTH: 922
<212> TYPE: PRT
<213> ORGANISM: Artificial Sequence
<220> FEATURE:
<223> OTHER INFORMATION: Synthetic amino acid sequence

<400> SEQUENCE: 8

```
Met Lys Thr Ile Ile Ile Asn Gly Val Gln Phe Asn Thr Asp Glu Asp
1               5                   10                  15

Thr Thr Ile Leu Lys Phe Ala Arg Asp Asn Asn Ile Asp Ile Ser Ala
            20                  25                  30

Leu Cys Phe Leu Asn Asn Cys Asn Asn Asp Ile Asn Lys Cys Glu Ile
        35                  40                  45

Cys Thr Val Glu Val Glu Gly Thr Gly Leu Val Thr Ala Cys Asp Thr
    50                  55                  60

Leu Ile Glu Asp Gly Met Ile Ile Asn Thr Asn Ser Asp Ala Val Asn
65                  70                  75                  80

Glu Lys Ile Lys Ser Arg Ile Ser Gln Leu Leu Asp Ile His Glu Phe
                85                  90                  95

Lys Cys Gly Pro Cys Asn Arg Arg Glu Asn Cys Glu Phe Leu Lys Leu
            100                 105                 110
```

-continued

```
Val Ile Lys Tyr Lys Ala Arg Ala Ser Lys Pro Phe Leu Pro Lys Asp
            115                 120                 125
Lys Thr Glu Tyr Val Asp Glu Arg Ser Lys Ser Leu Thr Val Asp Arg
        130                 135                 140
Thr Lys Cys Leu Leu Cys Gly Arg Cys Val Asn Ala Cys Gly Lys Asn
145                 150                 155                 160
Thr Glu Thr Tyr Ala Met Lys Phe Leu Asn Lys Asn Gly Lys Thr Ile
                165                 170                 175
Ile Gly Ala Glu Asp Glu Lys Cys Phe Asp Asp Thr Asn Cys Leu Leu
            180                 185                 190
Cys Gly Gln Cys Ile Ile Ala Cys Pro Val Ala Ala Leu Ser Glu Lys
        195                 200                 205
Ser His Met Asp Arg Val Lys Asn Ala Leu Asn Ala Pro Glu Lys His
    210                 215                 220
Val Ile Val Ala Met Ala Pro Ser Val Arg Ala Ser Ile Gly Glu Leu
225                 230                 235                 240
Phe Asn Met Gly Phe Gly Val Asp Val Thr Gly Lys Ile Tyr Thr Ala
                245                 250                 255
Leu Arg Gln Leu Gly Phe Asp Lys Ile Phe Asp Ile Asn Phe Gly Ala
            260                 265                 270
Asp Met Thr Ile Met Glu Glu Ala Thr Glu Leu Val Gln Arg Ile Glu
        275                 280                 285
Asn Asn Gly Pro Phe Pro Met Phe Thr Ser Cys Cys Pro Gly Trp Val
    290                 295                 300
Arg Gln Ala Glu Asn Tyr Tyr Pro Glu Leu Leu Asn Asn Leu Ser Ser
305                 310                 315                 320
Ala Lys Ser Pro Gln Gln Ile Phe Gly Thr Ala Ser Lys Thr Tyr Tyr
                325                 330                 335
Pro Ser Ile Ser Gly Leu Asp Pro Lys Asn Val Phe Thr Val Thr Val
            340                 345                 350
Met Pro Cys Thr Ser Lys Lys Phe Glu Ala Asp Arg Pro Gln Met Glu
        355                 360                 365
Lys Asp Gly Leu Arg Asp Ile Asp Ala Val Ile Thr Thr Arg Glu Leu
    370                 375                 380
Ala Lys Met Ile Lys Asp Ala Lys Ile Pro Phe Ala Lys Leu Glu Asp
385                 390                 395                 400
Ser Glu Ala Asp Pro Ala Met Gly Glu Tyr Ser Gly Ala Gly Ala Ile
                405                 410                 415
Phe Gly Ala Thr Gly Gly Val Met Glu Ala Ala Leu Arg Ser Ala Lys
            420                 425                 430
Asp Phe Ala Glu Asn Ala Glu Leu Glu Asp Ile Glu Tyr Lys Gln Val
        435                 440                 445
Arg Gly Leu Asn Gly Ile Lys Glu Ala Glu Val Glu Ile Asn Asn Asn
    450                 455                 460
Lys Tyr Asn Val Ala Val Ile Asn Gly Ala Ser Asn Leu Phe Lys Phe
465                 470                 475                 480
Met Lys Ser Gly Met Ile Asn Glu Lys Gln Tyr His Phe Ile Glu Val
                485                 490                 495
Met Ala Cys His Gly Gly Cys Val Asn Gly Gly Gly Gln Pro His Val
            500                 505                 510
Asn Pro Lys Asp Leu Glu Lys Val Asp Ile Lys Lys Val Arg Ala Ser
        515                 520                 525
Val Leu Tyr Asn Gln Asp Glu His Leu Ser Lys Arg Lys Ser His Glu
```

```
                530                 535                 540
Asn Thr Ala Leu Val Lys Met Tyr Gln Asn Tyr Phe Gly Lys Pro Gly
545                 550                 555                 560

Glu Gly Arg Ala His Glu Ile Leu His Phe Lys Tyr Lys Lys Gly Ser
                565                 570                 575

Ala Gly Ser Ala Gly Ser Ala Gly Ser Ala Gly Ser Ala Gly Ser Ala
                580                 585                 590

Gly Ser Ala Gly Ser Ala Gly Ser Ala Gly Ser Ala Gly Ser Ala Gly
                595                 600                 605

Ser Ala Gly Ser Ala Gly Ser Ala Gly Ser Ala Thr Gln Ala Lys Ala
                610                 615                 620

Lys His Ala Asp Val Pro Val Asn Leu Tyr Arg Pro Asn Ala Pro Phe
625                 630                 635                 640

Ile Gly Lys Val Ile Ser Asn Glu Pro Leu Val Lys Glu Gly Gly Ile
                645                 650                 655

Gly Ile Val Gln His Ile Lys Phe Asp Leu Thr Gly Gly Asn Leu Lys
                660                 665                 670

Tyr Ile Glu Gly Gln Ser Ile Gly Ile Ile Pro Pro Gly Val Asp Lys
                675                 680                 685

Asn Gly Lys Pro Glu Lys Leu Arg Leu Tyr Ser Ile Ala Ser Thr Arg
                690                 695                 700

His Gly Asp Asp Val Asp Asp Lys Thr Ile Ser Leu Cys Val Arg Gln
705                 710                 715                 720

Leu Glu Tyr Lys His Pro Glu Ser Gly Glu Thr Val Tyr Gly Val Cys
                725                 730                 735

Ser Thr Tyr Leu Thr His Ile Glu Pro Gly Ser Glu Val Lys Ile Thr
                740                 745                 750

Gly Pro Val Gly Lys Glu Met Leu Leu Pro Asp Asp Pro Glu Ala Asn
                755                 760                 765

Val Ile Met Leu Ala Thr Gly Thr Gly Ile Ala Pro Met Arg Thr Tyr
                770                 775                 780

Leu Trp Arg Met Phe Lys Asp Ala Glu Arg Ala Ala Asn Pro Glu Tyr
785                 790                 795                 800

Gln Phe Lys Gly Phe Ser Trp Leu Val Phe Gly Val Pro Thr Thr Pro
                805                 810                 815

Asn Ile Leu Tyr Lys Glu Glu Leu Glu Glu Ile Gln Gln Lys Tyr Pro
                820                 825                 830

Asp Asn Phe Arg Leu Thr Tyr Ala Ile Ser Arg Glu Gln Lys Asn Pro
                835                 840                 845

Gln Gly Gly Arg Met Tyr Ile Gln Asp Arg Val Ala Glu His Ala Asp
850                 855                 860

Glu Leu Trp Gln Leu Ile Lys Asn Gln Lys Thr His Thr Tyr Ile Cys
865                 870                 875                 880

Gly Leu Arg Gly Met Glu Glu Gly Ile Asp Ala Ala Leu Ser Ala Ala
                885                 890                 895

Ala Ala Lys Glu Gly Val Thr Trp Ser Asp Tyr Gln Lys Asp Leu Lys
                900                 905                 910

Lys Ala Gly Arg Trp His Val Glu Thr Tyr
                915                 920

<210> SEQ ID NO 9
<211> LENGTH: 19
<212> TYPE: PRT
<213> ORGANISM: Artificial Sequence
```

```
<220> FEATURE:
<223> OTHER INFORMATION: Synthetic amino acid sequence

<400> SEQUENCE: 9

Leu Gly Gly Gly Gly Ser Gly Gly Gly Ser Gly Gly Gly Ser
1               5                   10                  15

Ala Ala Ala

<210> SEQ ID NO 10
<211> LENGTH: 20
<212> TYPE: PRT
<213> ORGANISM: Artificial Sequence
<220> FEATURE:
<223> OTHER INFORMATION: Synthetic amino acid sequence

<400> SEQUENCE: 10

Leu Ala Glu Ala Ala Ala Lys Glu Ala Ala Ala Lys Glu Ala Ala Ala
1               5                   10                  15

Lys Ala Ala Ala
            20

<210> SEQ ID NO 11
<211> LENGTH: 15
<212> TYPE: PRT
<213> ORGANISM: Artificial Sequence
<220> FEATURE:
<223> OTHER INFORMATION: Synthetic amino acid sequence

<400> SEQUENCE: 11

Leu Ala Glu Ala Ala Ala Lys Glu Ala Ala Ala Lys Ala Ala Ala
1               5                   10                  15

<210> SEQ ID NO 12
<211> LENGTH: 25
<212> TYPE: PRT
<213> ORGANISM: Artificial Sequence
<220> FEATURE:
<223> OTHER INFORMATION: Synthetic amino acid sequence

<400> SEQUENCE: 12

Leu Ser Gly Gly Gly Gly Ser Gly Gly Gly Ser Gly Gly Gly Gly
1               5                   10                  15

Ser Gly Gly Gly Gly Ser Ala Ala Ala
            20                  25

<210> SEQ ID NO 13
<211> LENGTH: 25
<212> TYPE: PRT
<213> ORGANISM: Artificial Sequence
<220> FEATURE:
<223> OTHER INFORMATION: Synthetic amino acid sequence

<400> SEQUENCE: 13

Leu Ala Glu Ala Ala Ala Lys Glu Ala Ala Ala Lys Glu Ala Ala Ala
1               5                   10                  15

Lys Glu Ala Ala Ala Lys Ala Ala Ala
            20                  25
```